(12) United States Patent
Hagen et al.

(10) Patent No.: US 9,962,705 B2
(45) Date of Patent: *May 8, 2018

(54) METHOD AND APPARATUS FOR EFFECTING AUTOMATED MOVEMENT OF A MAGNET IN AN INSTRUMENT FOR PERFORMING A MAGNETIC SEPARATION PROCEDURE

(71) Applicant: GEN-PROBE INCORPORATED, San Diego, CA (US)

(72) Inventors: Norbert D. Hagen, Carlsbad, CA (US); Byron J. Knight, San Diego, CA (US); David Opalsky, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/669,419

(22) Filed: Mar. 26, 2015

(65) Prior Publication Data
US 2015/0196915 A1 Jul. 16, 2015

Related U.S. Application Data

(62) Division of application No. 12/781,390, filed on May 17, 2010, now Pat. No. 9,011,771.

(Continued)

(51) Int. Cl.
*B01L 3/00* (2006.01)
*B01L 9/00* (2006.01)
(Continued)

(52) U.S. Cl.
CPC ............... *B01L 3/52* (2013.01); *B01L 3/561* (2013.01); *B01L 9/52* (2013.01); *B03C 1/0332* (2013.01);
(Continued)

(58) Field of Classification Search
CPC ..... G01N 2035/00524; G01N 35/0098; G01N 35/1065; B01L 3/0279
See application file for complete search history.

(56) References Cited

U.S. PATENT DOCUMENTS

| 4,675,299 A | 6/1987 | Witty et al. |
| 4,895,650 A | 1/1990 | Wang |

(Continued)

FOREIGN PATENT DOCUMENTS

| CN | 101002099 A | 7/2007 |
| CN | 201096779 Y | 8/2008 |

(Continued)

OTHER PUBLICATIONS

USPTO Office Action, U.S. Appl. No. 14/487,580, dated Nov. 17, 2015.

(Continued)

*Primary Examiner* — P. Kathryn Wright
(74) *Attorney, Agent, or Firm* — Rothwell, Figg, Ernst & Manbeck, P.C.; Charles B. Cappellari

(57) ABSTRACT

Methods, systems, and apparatus are provided for automated isolation of selected analytes, to which magnetically-responsive solid supports are bound, from other components of a sample. An apparatus for performing an automated magnetic separation procedure includes a mechanism for effecting linear movement of a magnet between operative and non-operative positions with respect to a receptacle device. A receptacle holding station within which a receptacle device may be temporarily stored prior to moving the receptacle to the apparatus for performing magnetic separation includes magnets for applying a magnetic field to the receptacle device held therein, thereby drawing at least a portion of the magnetically-responsive solid supports out of suspension before the receptacle device is moved to the magnetic separation station. An automated receptacle transport (Continued)

mechanism moves the receptacle devices between the apparatus for performing magnetic separation and the receptacle holding station.

14 Claims, 17 Drawing Sheets

Related U.S. Application Data

(60) Provisional application No. 61/178,671, filed on May 15, 2009.

(51) Int. Cl.

| | |
|---|---|
| G01N 35/00 | (2006.01) |
| B03C 1/033 | (2006.01) |
| B03C 1/28 | (2006.01) |
| B65B 3/04 | (2006.01) |
| B03C 1/12 | (2006.01) |
| B03C 1/14 | (2006.01) |
| B25J 11/00 | (2006.01) |
| C12N 15/10 | (2006.01) |

(52) U.S. Cl.
CPC .............. *B03C 1/12* (2013.01); *B03C 1/14* (2013.01); *B03C 1/28* (2013.01); *B03C 1/286* (2013.01); *B03C 1/288* (2013.01); *B25J 11/00* (2013.01); *B65B 3/04* (2013.01); *C12N 15/1013* (2013.01); *G01N 35/0098* (2013.01); *B01L 2300/0609* (2013.01); *B01L 2300/12* (2013.01); *B03C 2201/18* (2013.01); *B03C 2201/26* (2013.01); *Y10T 29/49815* (2015.01)

(56) References Cited

U.S. PATENT DOCUMENTS

| | | | |
|---|---|---|---|
| 5,005,721 A | | 4/1991 | Jordan |
| 5,013,529 A | * | 5/1991 | Itoh .................. G01N 35/1067 422/511 |
| 5,098,663 A | | 3/1992 | Berthold et al. |
| D325,638 S | | 4/1992 | Sloat et al. |
| 5,200,084 A | | 4/1993 | Liberti et al. |
| 5,260,028 A | * | 11/1993 | Astle .................. G01N 1/405 210/635 |
| 5,363,885 A | | 11/1994 | McConnell et al. |
| 5,397,539 A | | 3/1995 | Hayashi et al. |
| 5,567,326 A | | 10/1996 | Ekenberg et al. |
| 5,647,994 A | * | 7/1997 | Tuunanen ............... B03C 1/288 210/222 |
| 5,722,553 A | | 3/1998 | Hovatter |
| 5,780,224 A | | 7/1998 | Collins |
| 5,875,533 A | | 3/1999 | Henry |
| 5,897,102 A | | 4/1999 | Sorkin |
| 6,143,578 A | | 11/2000 | Bendele et al. |
| 6,254,826 B1 | | 7/2001 | Acosta et al. |
| 6,284,113 B1 | | 9/2001 | Bjornson et al. |
| 6,335,166 B1 | | 1/2002 | Ammann et al. |
| 6,368,561 B1 | | 4/2002 | Rutishauser et al. |
| 6,421,898 B1 | | 7/2002 | Tsai |
| 6,447,729 B1 | | 9/2002 | Tuunanen |
| 6,558,628 B1 | | 5/2003 | Reo |
| 6,605,213 B1 | | 8/2003 | Ammann et al. |
| 6,672,458 B2 | | 1/2004 | Hansen et al. |
| 6,890,742 B2 | | 5/2005 | Ammann et al. |
| 7,360,984 B1 | | 4/2008 | Sugiyama et al. |
| 7,560,255 B2 | | 7/2009 | Ammann et al. |
| 7,632,405 B2 | | 12/2009 | Siddiqi |
| 7,941,904 B2 | | 5/2011 | Smith |
| 8,047,086 B2 | | 11/2011 | Smith |
| 8,276,762 B2 | | 10/2012 | Davis et al. |
| 8,580,574 B2 | | 11/2013 | Smith |
| 8,844,731 B2 | | 9/2014 | Davis et al. |
| 9,144,801 B2 | | 9/2015 | Johnson et al. |
| 9,618,139 B2 | | 4/2017 | Handique |
| 9,636,647 B2 | | 5/2017 | Vincent et al. |
| 2001/0019826 A1 | | 9/2001 | Ammann |
| 2002/0028489 A1 | | 3/2002 | Ammann et al. |
| 2002/0098117 A1 | | 7/2002 | Ammann et al. |
| 2003/0026733 A1 | | 2/2003 | Lacourt et al. |
| 2005/0130198 A1 | | 6/2005 | Ammann et al. |
| 2005/0155921 A1 | | 7/2005 | Siddiqut |
| 2007/0180935 A1 | * | 8/2007 | Angus .................. B01L 3/0279 73/864.14 |
| 2008/0268528 A1 | | 10/2008 | Ammann et al. |
| 2008/0311678 A1 | | 12/2008 | Ootani et al. |
| 2009/0095419 A1 | | 4/2009 | Ammann et al. |
| 2010/0233754 A1 | | 9/2010 | Guex |
| 2010/0284864 A1 | | 11/2010 | Holenstein et al. |
| 2011/0275087 A1 | | 11/2011 | Breidenthal et al. |
| 2011/0300621 A1 | | 12/2011 | Belz et al. |
| 2012/0282683 A1 | | 11/2012 | Mototsu |
| 2013/0043191 A1 | | 2/2013 | Park et al. |
| 2013/0079921 A1 | | 3/2013 | Fukuma et al. |
| 2013/0209334 A1 | | 8/2013 | Wilson et al. |
| 2013/0273552 A1 | | 10/2013 | Ohashi |
| 2016/0376137 A1 | | 12/2016 | Bell |
| 2017/0059562 A1 | | 3/2017 | Kawamoto et al. |

FOREIGN PATENT DOCUMENTS

| | | | |
|---|---|---|---|
| EP | 1726963 | A2 | 11/2006 |
| JP | 8-229414 | * | 9/1996 |
| JP | H08229414 | A | 9/1996 |
| JP | 10038897 | A | 2/1998 |
| JP | 11248714 | A | 9/1999 |
| JP | 2006112824 | A | 4/2006 |
| WO | 2005/044460 | A2 | 5/2005 |
| WO | WO 2005/044460 | A2 | 5/2005 |
| WO | 2005/065831 | A1 | 7/2005 |
| WO | WO 2005/065831 | A1 | 7/2005 |
| WO | 2007/063174 | A1 | 6/2007 |
| WO | WO 2007/063174 | A1 | 6/2007 |

OTHER PUBLICATIONS

International Search Report and Written Opinion in PCT/US2010/035138, 12 pages. (dated Aug. 9, 2010).
Notice of Allowance in co-pending U.S. Appl. No. 12/335,814, 12 pages, (dated Feb. 1, 2011).
Notice of Allowance issued in co-pending U.S. Appl. No. 12/335,812, 28 pages, (dated Jun. 27, 2011).
Non-final Office Action issued in co-pending U.S. Appl. No. 12/335.818, 42 pages, (dated Jul. 1, 2011).
USPTO Office Action, U.S. Appl. No. 12/781,425, dated Dec. 19, 2011.
USPTO Final Office Action, U.S. Appl. No. 12/781,425, dated Mar. 19, 2012.
Notice of Allowance issued in U.S. Appl. No. 14/487,580, 31 pages (dated Mar. 23, 2016).
Non-final Office Action issued in U.S. Appl. No. 14/669,531, 42 pages (dated Feb. 2, 2016).
Non-final Office Action issued in U.S. Appl. No. 14/500,584, 12 pages (dated Apr. 20, 2015).
Notice of Allowance issued in U.S. Appl. No. 14/500,584, 10 pages (dated Oct. 13, 2015).
Notice of Allowance issued in U.S. Appl. No. 12/781,425 (dated May 4, 2012).
Notice of Allowance issued in U.S. Appl. No. 12/781,425 (dated Aug. 17, 2012).
PCT International Preliminary Report of Patentability, International Application No. PCT/US2010/035138, 6 pages (dated Nov. 24, 2011).
EPO Communication pursuant to rules 161(1) and 162 EPC, European Patent Application No. 10719719.6, 2 pages (dated Dec. 22, 2011).
Communication pursuant to Article 94(3) EPC, European Application No. 10719719.6, 5 pages (dated Apr. 19, 2013).

(56) References Cited

OTHER PUBLICATIONS

SIPO Office Action with English Translation, Chinese Patent Application No. 201080020619.9, 11 pages (dated Oct. 27, 2015).
SIPO Search Report with English Translation, Chinese Patent Application No. 201080020619.9, 4 pages (dated Oct. 27, 2015).
USPTO Non-Final Office Action, U.S. Appl. No. 14/669,531, dated Jul. 20, 2016.
Final Office Action issued in U.S. Appl. No. 14/669,531, 18 pages (dated Dec. 29, 2016).
USPTO Notice of Allowance, U.S. Appl. No. 14/669,531, dated Mar. 17, 2017.
USPTO Non-Final Office Action, U.S. Appl. No. 14/996,339, dated May 12, 2017.
SIPO Office Action, Chinese Application No. 201511001054.0, dated Jul. 24, 2017.
SIPO Search Report, Chinese Application No. 201511001054.0, dated Jul. 6, 2017.
Final Office Action issued in U.S. Appl. No. 14/996,339, 55 pages (dated Nov. 24, 2017).

* cited by examiner

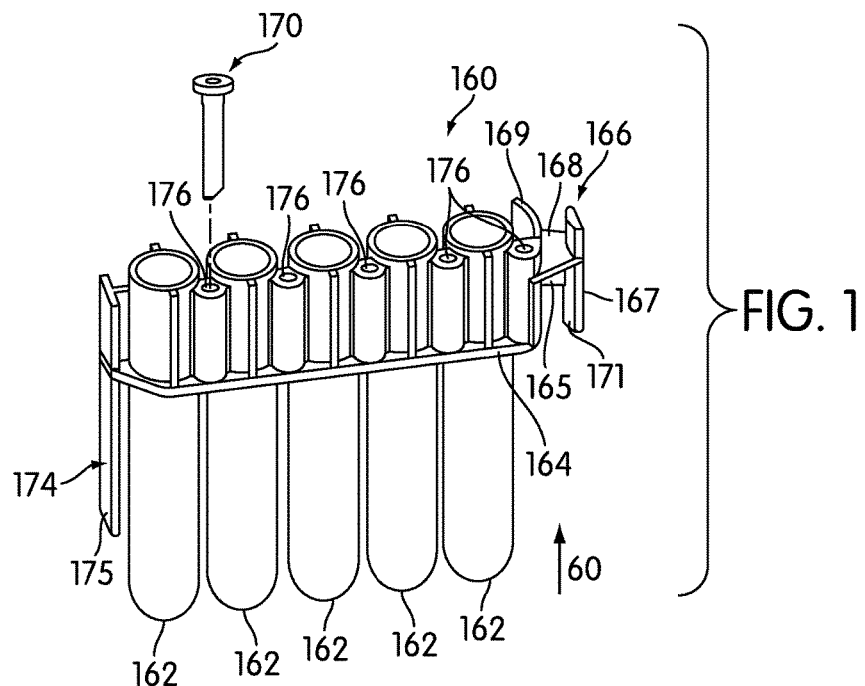
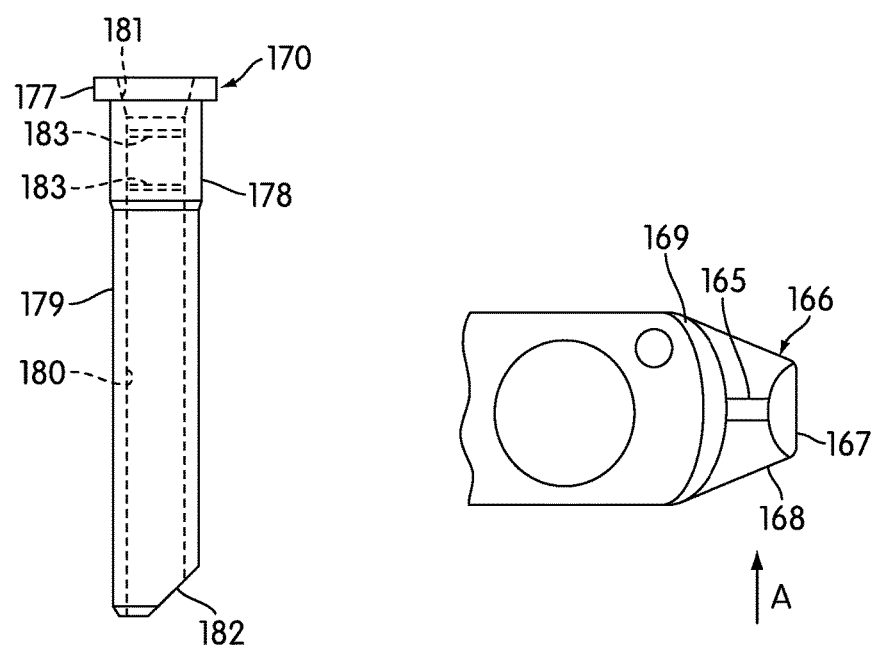
FIG. 1
FIG. 2
FIG. 3

METHOD AND APPARATUS FOR EFFECTING AUTOMATED MOVEMENT OF A MAGNET IN AN INSTRUMENT FOR PERFORMING A MAGNETIC SEPARATION PROCEDURE

CROSS-REFERENCE TO RELATED APPLICATIONS

This application claims the benefit under 35 U.S.C. §§ 120, 121 of U.S. patent application Ser. No. 12/781,390, filed May 17, 2010 which claims the benefit under 35 U.S.C. § 119(e) of U.S. Provisional Application No. 61/178,671, filed May 15, 2009, the respective disclosures of which are hereby incorporated by reference in their entireties.

BACKGROUND

Field of the Invention

The present invention relates to methods, systems, and apparatus for isolating and separating an analyte of interest (e.g., a target nucleic acid) from other components of a sample.

Background of the Invention

All documents referred to herein, or the indicated portions, are hereby incorporated by reference herein. No document, however, is admitted to be prior art to the claimed subject matter.

Nucleic acid test (NAT) procedures, and other forms of analyte detection, often require a sample preparation procedure for isolating and separating an analyte from other components of a sample having the potential to interfere with a test protocol. Many of these sample preparation procedures require immobilizing analyte on magnetically-responsive particles, which are then drawn out of suspension upon exposure to a magnetic force. The immobilization may be specific or non-specific for the analyte of interest. Once the magnetically-responsive particles are isolated within a receptacle, the non-isolated components of the sample may be aspirated and the magnetically-responsive particles resuspended in a fluid medium. This process can then be repeated one or more times to further purify the sample.

It is desirable, therefore, to have a compact, automated device for performing the isolation, aspiration and re-suspension steps of a sample preparation procedure in an analyzer, including structure for removing protective tips used in the aspiration step.

SUMMARY OF THE INVENTION

Aspects of the invention are embodied in an apparatus which includes a fluid transfer device and a slide comprising one or more conduit stripping elements. The fluid transfer device includes one or more aspirator probes, each aspirator probe having a distal end, and each distal end being adapted to have a conduit mounted thereon. Each stripping element of the slide is associated with a corresponding aspirator probe, and each stripping element is adapted to remove a conduit from the distal end of the associated aspirator probe. The slide is movable between a first position and a second position in the apparatus, such that when the slide is in the first position, no stripping element is in a position to engage the associated aspirator probe to strip the conduit mounted thereon, and when the slide is in the second position, each stripping element is in a position to engage the associated aspirator probe to strip the conduit mounted thereon.

In one embodiment, the apparatus further includes one or more magnets carried by the slide.

In one embodiment, the apparatus further includes a receptacle carrier configured to carry a receptacle device in an operative position with respect to the aspirator probes, and the receptacle carrier is constructed and arranged to selectively impart an orbital motion to a receptacle device carried by the receptacle carrier.

In one embodiment, the fluid transfer device includes a plurality of aspirator probes, and the receptacle device includes a plurality of receptacles, each receptacle being associated with one of the aspirator probes.

In one embodiment, the fluid transfer device further includes a probe moving mechanism adapted to move the plurality of aspirator probes in unison with respect to the associated receptacles.

In one embodiment, the apparatus further includes a guide structure for supporting the slide for translation between the first and second positions and a slide moving mechanism adapted to effect powered movement of the slide between the first and second positions.

In one embodiment, the slide moving mechanism includes a motor, a threaded drive screw coupled to an output shaft of the motor, and a screw follower mounted to the slide. The drive screw is engaged with the screw follower such that powered rotation of the drive screw by the motor causes translation of the slide.

In one embodiment, the slide moving mechanism includes a motor with a drive pulley mounted to an output shaft thereof, an idler pulley, and a drive belt carried on the drive pulley and the idler pulley and coupled to the slide to transfer powered rotation of the drive pulley to translation of the slide.

In one embodiment, the apparatus further includes a plurality of the aspirator probes, and the slide comprises a plurality of stripping elements. The stripping elements are arranged in a staggered configuration so that when the plurality of aspirator probes are moved with respect to the plurality of stripping elements, the stripping elements sequentially remove the conduits from the associated aspirator probes one at a time.

Other aspects of the invention are embodied in an apparatus that includes a receptacle carrier, a fluid transfer device, and a magnet moving apparatus. The receptacle carrier is configured to carry a receptacle containing a solution which includes magnetically-responsive solid supports and to carry the receptacle throughout a fluid transfer process. The fluid transfer device includes a plurality of aspirator probes. The receptacle carrier is constructed and arranged to selectively impart a motion to a receptacle carried by the receptacle carrier to mix the contents of the receptacle and to selectively move the receptacle between a first position with respect to the fluid transfer device and a second position with respect to the fluid transfer device. The magnet moving apparatus includes at least one magnet generating a magnetic field and is constructed and arranged to effect linear translation of the magnet between an operational position with respect to the receptacle carried in the receptacle carrier and a non-operational position with respect to the receptacle carried in the receptacle carrier. The magnetic field draws the magnetically-responsive solid supports to an inner surface of the receptacle adjacent to the magnet when the at least one magnet is in the operational position, and the effect of the magnetic field on the magnetically-responsive solid supports is less when the magnet is in the non-operational position than when the magnet is in the operational position. When the receptacle is positioned in the first position with respect to the fluid transfer device, it interferes with translation of the magnet moving apparatus from the non-operational position to the operational position.

In one embodiment, the receptacle carrier is constructed and arranged to impart an orbital motion to the receptacle device carried thereby.

In one embodiment, the fluid transfer device further comprises a probe moving mechanism adapted to move the plurality of probes in unison with respect to the receptacle carrier. The probe moving mechanism and the receptacle carrier are constructed and arranged so that movement of the plurality of probes with respect to the receptacle carrier when the receptacle carrier is in the first position will cause the distal end of each probe to engage an associated conduit carried on a receptacle device carried by the receptacle carrier so that a conduit becomes mounted on the distal end of each probe.

In one embodiment, the magnet moving apparatus comprises a plurality of stripping elements. Each stripping element is associated with a corresponding aspirator probe, and is adapted to remove a conduit from the distal end of the associated aspirator probe. When the magnet moving apparatus is in the operational position, each stripping element is in a position to engage the associated aspirator probe to strip the conduit mounted thereon, and when the magnet moving apparatus is in the non-operational position, no stripping element is in a position to engage the associated aspirator probe to strip the conduit mounted thereon.

In one embodiment, the magnet moving apparatus includes a magnet carrier configured to carry the magnet, a motor, a threaded drive screw coupled to an output shaft of the motor, and a screw follower mounted to the magnet carrier. The drive screw is engaged with the screw follower such that powered rotation of the drive screw by the motor causes translation of the magnet carrier.

In one embodiment, the magnet moving apparatus includes a magnet carrier configured to carry the magnet, a motor with a drive pulley mounted to an output shaft thereof, an idler pulley, and a drive belt carried on the drive pulley and the idler pulley and coupled to the magnet carrier to transfer powered rotation of the drive pulley to translation of the magnet carrier.

Further aspects of the invention are embodied in a method for removing a conduit from a distal end of each of a plurality of fluid transfer probes. A slide is moved by powered translation in a direction transverse to the axes of the probes from a first location to a second location. When the slide is in the first location, no portion of the slide is in a position to be engaged by any of the probes, and when the slide is in the second location, conduit-stripping portions of the slide are in positions to be engaged by the distal ends of the probes. With the slide in the second position, the probes are moved axially with respect to the slide to engage the distal ends of the probes with the conduit-stripping portions of the slide to strip the conduits from the probes.

In one embodiment, stripping the conduits from the distal ends of the probes includes moving the probes in an axial direction toward the slide until the conduits disposed on the distal ends of the probes engage the conduit-stripping portions of the slide and then moving the probes in an opposite axial direction away from the slide while retaining the conduits with the conduit-stripping portions of the slide to pull the conduits from the distal ends of the probes.

In one embodiment, retaining the conduits with the conduit-stripping portions of the slide providing, for each conduit-stripping portion, a key-hole opening having a first portion with a transverse size sufficient to permit the conduit to pass therethrough and a second portion with a transverse size sufficient to permit the probe to pass therethrough, but not sufficient to permit the conduit to pass therethrough. The distal end of the probe with the conduit disposed thereon is passed through the first portion of the key-hole opening. Relative movement between the probe and the slide is effected so that the probe is in the second portion of the key-hole opening. The probe is then withdrawn from the key-hole opening while the conduit is retained by the conduit-stripping portion when the conduit is unable to pass through the second portion of the key-hole opening.

In one embodiment, each of the conduits is sequentially retained during axial movement of the probes away from the slide so that all conduits are not pulled from the distal ends of the probes simultaneously.

In one embodiment, one or more magnets is mounted on the slide such that, when the slide is in the first location, the magnets have substantially no effect on magnetically-responsive solid supports contained in a receptacle device positioned so as to be engageable by the probes, and when the slide is in the second location, the magnets are positioned adjacent to the receptacle device so that the magnets will draw at least a portion of the magnetically-responsive solid supports to a wall of the receptacle device.

In one embodiment, the magnetically-responsive solids supports are adapted to immobilize an analyte thereon.

Other aspects of the invention are embodied in a system for separating an analyte of interest from other components of a sample contained in a receptacle. The system includes a receptacle holding station and a magnetic separation station. The receptacle holding station is configured to receive and hold a receptacle delivered to the receptacle holding station by a receptacle transport and includes one or more stationary magnets positioned to apply a magnetic field to the contents of the receptacle held in the receptacle holding station. The magnetic separation station comprises one or more magnets and is constructed and arranged to perform a magnetic separation procedure on the contents of a receptacle transported from the receptacle holding station to the magnetic separation station by a receptacle transport by magnetically isolating an analyte immobilized on a magnetically-responsive solid support and removing other components of the sample from the receptacle.

In one embodiment, the system further includes a receptacle transport configured to automatically move the receptacle between the receptacle holding station and the magnetic separation station.

In one embodiment, the receptacle holding station is configured to receive and hold a receptacle device comprising a plurality of individual receptacles.

In one embodiment, the receptacle holding station is configured to receive and hold at least two receptacle devices.

In one embodiment, the receptacle holding station includes a base block, two or more walls extending upwardly from the base block, and a shroud partially covering the two or more walls and defining a receptacle slot between each adjacent pair of walls. In one embodiment, the receptacle holding station comprises a first wall, a second wall, and a third wall extending upwardly from the base block and defining a first receptacle slot between the first and second walls and a second receptacle slot between the second and third walls.

In one embodiment, the base block of the receptacle holding station is made from plastic.

In one embodiment, the receptacle holding station further includes a resilient receptacle retaining element within each receptacle slot and configured to releasably retain a receptacle within each receptacle slot.

In one embodiment, each of the resilient receptacle retaining elements includes a clip disposed within a clip recess formed in one wall of each pair of walls defining a receptacle slot.

In one embodiment, the receptacle holding station further includes a magnet subassembly attached to one wall of each pair of walls defining a receptacle slot. The magnet subassembly includes a plurality of magnets, an upper holder plate disposed within holder plate grooves formed within the top surface of each of the magnets and which includes a separating projection at each end thereof and between adjacent magnets to hold each magnet within its respective position, and a lower holder plate disposed within holder plate grooves formed in the lower surfaces of the magnets and which includes a separating projection at opposite ends thereof and between the adjacent magnets to hold each magnet within its respective position.

In one embodiment, each of the magnets has a generally solid, rectangular shape.

In one embodiment, the magnetic separation station includes a magnet moving apparatus constructed and arranged to move the one or more magnets between a first position in which the magnets have substantially no effect on the magnetically-responsive solid supports contained within the receptacle and a second position in which the magnets cause the solid supports to become isolated within the receptacle.

Other aspects of the invention are embodied in a method for separating an analyte of interest from other components of a sample contained in a receptacle. At a first location, a receptacle containing magnetically-responsive solid supports dispersed in a fluid medium comprising a sample material is exposed to a first magnetic field, thereby isolating the solid supports within the receptacle. The solid supports are adapted to immobilize an analyte thereon. The receptacle is then transferred to a second location. At the second location, the contents of the receptacle are subjected to a second magnetic field, thereby isolating the solid supports within the receptacle, the fluid contents of the receptacle are removed from the isolated solid supports, the second magnetic field is then removed, a suspension fluid is dispensed into the receptacle, and the solid supports are re-suspended.

In one embodiment, steps occurring at the second location are repeated one or more times.

In one embodiment, after repeating the steps one or more times, the receptacle is removed from the second location.

In one embodiment, the first location comprises a receptacle holding station configured to receive and hold the receptacle and includes one or more stationary magnets constructed and arranged to apply the first magnetic field to the contents of the receptacle held in the receptacle holding station In one embodiment, the second location comprises a magnetic separation station constructed and arranged to perform a magnetic separation procedure on the receptacle by positioning magnets to magnetically isolate the magnetically-responsive solid support and then removing the fluid medium from the receptacle.

In one embodiment, the transferring step comprises withdrawing the receptacle from the first location with an automated receptacle transport, carrying the receptacle with the receptacle transport from the first location to the second location, and depositing the receptacle at the second location with the receptacle transport.

In one embodiment, the solid supports remain substantially isolated within the receptacle during the transfer from the first location to the second location.

These and other features, aspects, and advantages of the present invention will become apparent to those skilled in the art after considering the following detailed description, appended claims and accompanying drawings.

DESCRIPTION OF THE DRAWINGS

FIG. 1 is a perspective view of a reaction receptacle in the form of a multiple receptacle device employed in combination with an apparatus embodying aspects of the present invention;

FIG. 2 is a side elevation of a contact-limiting tip employed in combination with an instrument for performing a magnetic separation procedure and carried on the multiple receptacle device shown in FIG. 1;

FIG. 3 is an enlarged bottom view of a portion of the multiple receptacle device, viewed in the direction of arrow "60" in FIG. 1;

DETAILED DESCRIPTION OF THE PREFERRED EMBODIMENT

Samples often include or are treated to release materials capable of interfering with the detection of an analyte (e.g., a targeted nucleic acid). To remove these interfering materials, samples can be treated with a target capture reagent that includes a magnetically-responsive solid support for immobilizing the analyte. See, e.g., U.S. Pat. Nos. 4,486, 539, 4,751,177, 5,288,609, 5,780,224, 6,433,160, and 6,534, 273. Suitable solid supports are paramagnetic particles (0.7-1.05 micron particles, Sera-Mag™ MG-CM, available from Seradyn, Inc., Indianapolis, Ind., as Cat. No. 24152105-050450) with covalently bound oligo$(dT)_{14}$. When the solid supports are brought into close proximity to a magnetic force, the solid supports are drawn out of suspension and aggregate adjacent a surface of a sample holding container, thereby isolating any immobilized analyte within the container. Non-immobilized materials in the sample can then be aspirated or otherwise separated from immobilized analyte. One or more wash steps may be performed to further purify the analyte.

Figure 4:
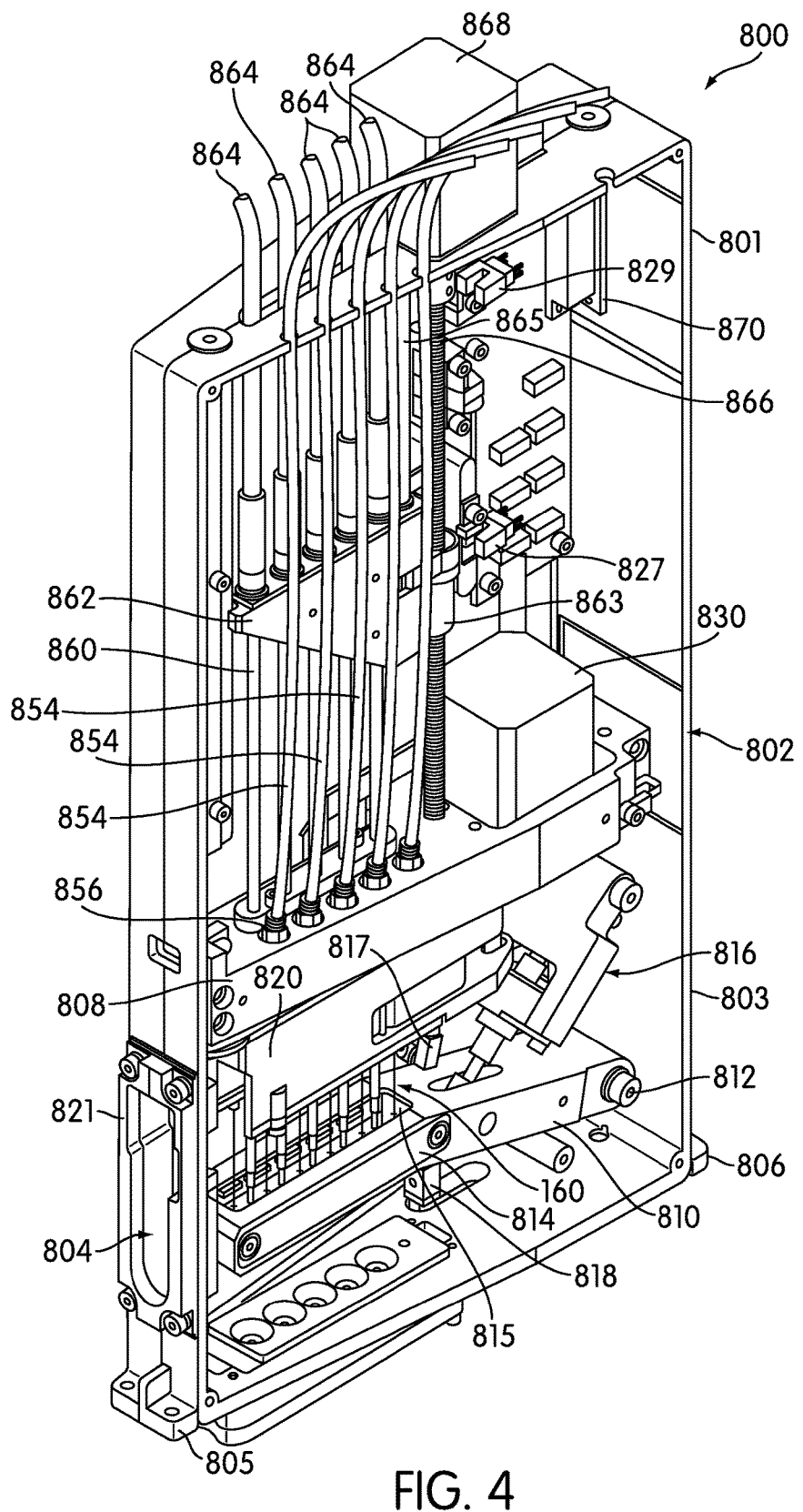
FIG. 4 is a perspective view of a magnetic separation station with a side plate thereof removed.

Methods, systems, and apparatus for performing a procedure for isolating and separating an analyte of interest from other components of a sample are embodied in a magnetic separation station, an embodiment of which is shown in FIG. 4. The magnetic separation station comprises a housing configured to receive a reaction receptacle which contains a sample material and a target capture reagent including magnetically-responsive solid supports adapted to directly or indirectly bind to an analyte of interest, such as a nucleic acid, that may be present in the sample. Details of an exemplary reaction receptacle and sample preparation procedures are described in more detail below.

The magnetic separation station includes magnets for attracting the magnetically-responsive solid supports to a side wall of the reaction receptacle and apparatus for selectively moving the magnets between a first position in which the magnets have substantially no effect on the magnetically-responsive solid supports contained within the reaction receptacle and a second position in which the magnets draw the magnetically-responsive solid supports to a side wall of the reaction receptacle. In particular embodiments, the apparatus for selectively moving the magnets is configured to effect a linear translation of the magnets between the first and the second positions. Such an apparatus may comprise a sled on which the magnets are carried and which may be actuated for linear translation by a belt or a threaded rod driven by a motor. The magnetic separation station further includes apparatus for aspirating fluids from a reaction receptacle held in the station, apparatus for dispensing fluids into the reaction receptacle, and apparatus for agitating the reaction receptacle to re-suspend magnetically-responsive solid supports and other materials following the aspirating and dispensing steps. The apparatus for aspirating fluids from the reaction receptacles may include aspirator tubes, and removable protective tips may be placed on the ends of the aspirator tubes and exchanged for new tips after each reaction receptacle is processed by the magnetic separation station to prevent contamination from one reaction receptacle to the next. The apparatus for effecting linear movement of the magnets may include tip removal elements adapted for removing the tips from the aspirator tubes after each receptacle is processed by the magnetic separation station.

A reaction receptacle containing sample material and a target capture reagent that includes magnetically-responsive solid supports is placed into the magnetic separation station, and the magnets are moved from the first, non-affecting position to the second position adjacent to the reaction receptacle. The magnets are held in the second position for a specified dwell time to draw magnetically-responsive solid supports to the side of the reaction receptacle. After the specified dwell time, with the magnets still in the second position, the fluid contents of the reaction receptacle are aspirated from the receptacle. A wash solution or other suspending fluid is then dispensed into the reaction receptacle, the magnets are moved back to the first position, and the reaction receptacle is agitated to rinse the magnetically-responsive solid supports from the reaction receptacle wall and re-suspend the magnetically-responsive solid supports. The magnets are then moved back to the second position to draw the magnetically-responsive solid supports to the walls of the reaction receptacle and out of suspension. This process of applying a magnetic force for a specified dwell time, aspirating fluid from the reaction receptacle, and re-suspending the magnetically-responsive solid supports may be repeated a specified number of times.

The magnetic separation station may be part of an instrument including various modules configured to receive one or more reaction receptacles within which is performed one or more steps of a multi-step analytical process, such as a nucleic acid test (NAT), or other chemical, biochemical or biological process. The instrument may further include a transfer apparatus configured to transfer reaction receptacles between the various modules, including transporting reaction receptacles into and out of the magnetic separation station. The instrument and each individual component, such as the magnetic separation station, is automated and may be controlled by an instrument control module including a microprocessor executing an instrument control program stored thereon.

Further details of the magnetic separation station are described below.

Figure 16:
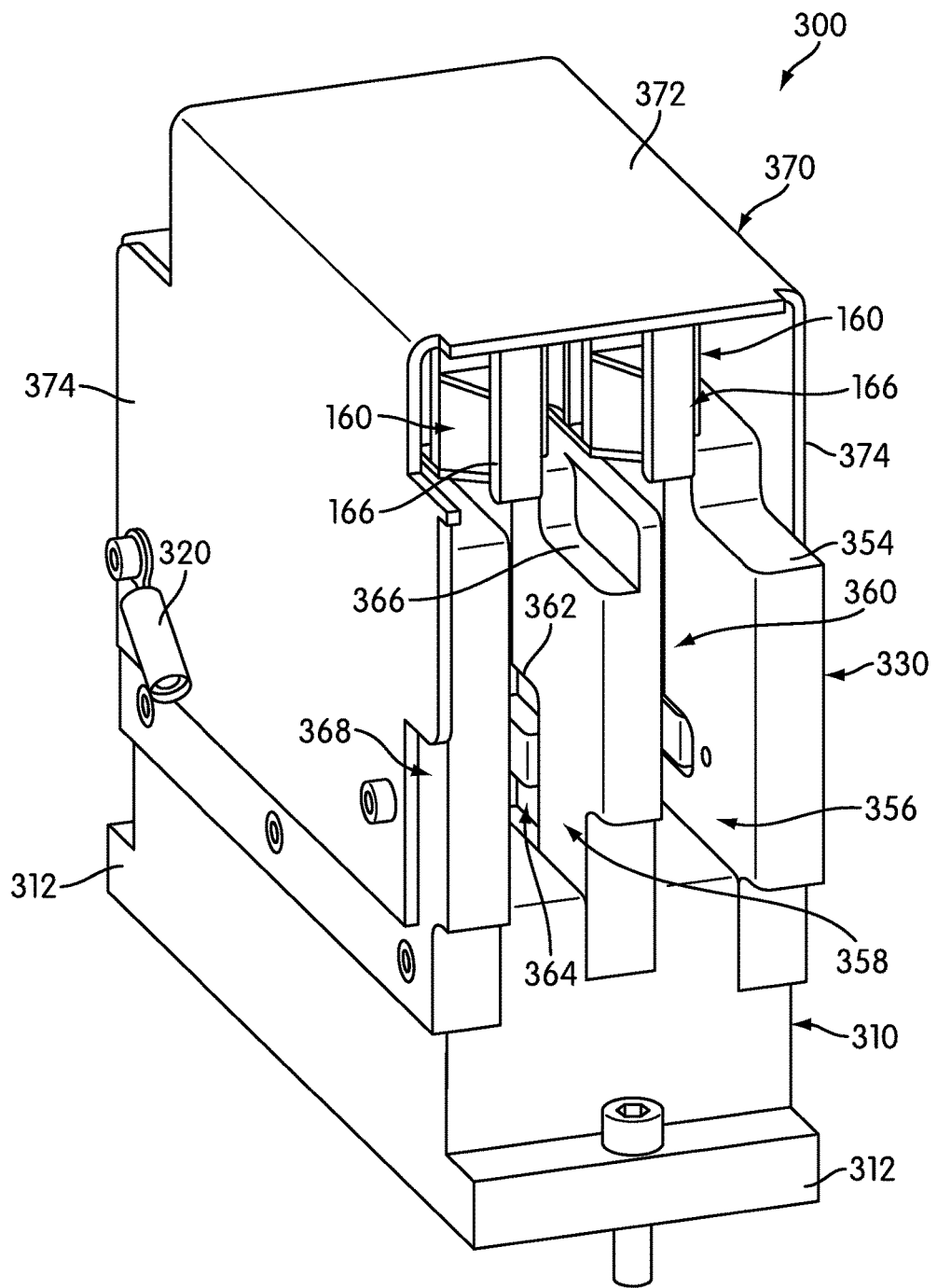
FIG. 16 is a front perspective view of a magnetic receptacle holding station for reaction receptacles.

Other aspects of the invention are embodied in a magnetic receptacle holding station, an embodiment of which is shown in FIG. 16. The receptacle holding station comprises a structure configured for receiving and temporarily holding a reaction receptacle in a stationary position. The receptacle holding station includes magnets configured so as to be positioned adjacent to the reaction receptacle when the receptacle is held within the receptacle holding station. A reaction receptacle containing sample material to which magnetically-responsive solid supports have been added can be placed into the receptacle holding station for a specified dwell time prior to moving the reaction receptacle into the magnetic separation station. The magnetically-responsive solid supports will be drawn to the side wall of the reaction receptacle to form an aggregate of solid supports prior to the receptacle being placed in the magnetic separation station, thus reducing at least the first magnetic dwell time required within the magnetic separation station.

Further details of the magnetic receptacle holding station are described below.

Multiple Receptacle Devices

As shown in FIG. 1, a reaction receptacle in the form of a multiple receptacle device ("MRD") 160 that can be used in conjunction with the magnetic separation station and the magnetic receptacle holding station of the present invention comprises a plurality of individual receptacles 162, preferably five. Other types of receptacle devices can be used in conjunction with the magnetic separation and magnetic receptacle holding stations, including devices comprising a single, individual receptacle. In the illustrated embodiment, the receptacles 162 are in the form of cylindrical tubes with open top ends and closed bottom ends and are connected to one another by a connecting rib structure 164 which defines a downwardly facing shoulder extending longitudinally along either side of the MRD 160. In the illustrated embodiment of the MRD 160, all of the receptacles 162 are substantially identical in size and shape. In other embodiments, the MRD 160 may include receptacles of varying sizes and shapes, which can be configured for use with the magnetic separation and magnetic receptacle holding stations.

In one embodiment, the MRD 160 is formed from injection molded polypropylene, such as that manufactured by Flint Hills Resources as product number P5M6K-048.

An arcuate shield structure 169 is provided at one end of the MRD 160. An MRD manipulating structure 166 extends from the shield structure 169. The manipulating structure is adapted to be engaged by a transport mechanism for moving the MRD 160 between different locations or modules of an instrument. Exemplary transport mechanisms that are compatible with the MRD 160 are described in U.S. Pat. No. 6,335,166 and in U.S. Provisional Application No. 61/178, 728 and corresponding non-provisional U.S. application Ser. No. 12/781,241. MRD manipulating structure 166 comprises a laterally extending plate 168 extending from shield structure 169 with a vertically extending piece 167 on the opposite end of the plate 168. A gusset wall 165 extends downwardly from lateral plate 168 between shield structure 169 and vertical piece 167.

As shown in FIG. 3, the shield structure 169 and vertical piece 167 have mutually facing convex surfaces. The MRD 160 may be engaged by a transport mechanism and other components, by moving an engaging member laterally (in the direction "A") into the space between the shield structure 169 and the vertical piece 167. The convex surfaces of the shield structure 169 and vertical piece 167 provide for wider points of entry for an engaging member undergoing a lateral relative motion into the space.

A label-receiving structure 174 having a flat label-receiving surface 175 is provided on an end of the MRD 160 opposite the shield structure 169 and MRD manipulating structure 166. Human and/or machine-readable labels, such as scannable bar codes, can be placed on the surface 175 to provide identifying and instructional information on the MRD 160.

The MRD 160 preferably includes tip holding structures 176 adjacent the open mouth of each respective receptacle 162. Each tip holding structure 176 provides a cylindrical orifice within which is received a conduit, such as contact-limiting tip 170, that is adapted to be placed onto the end of an aspirator tube 860. The construction and function of the tip 170 will be described below. Each holding structure 176 can be constructed and arranged to frictionally receive a tip 170 in a manner that prevents the tip 170 from falling out of the holding structure 176 when the MRD 160 is inverted, but permits the tip 170 to be removed from the holding structure 176 when engaged by an aspirator tube 860.

As shown in FIG. 2, the tip 170 comprises a generally cylindrical structure having a peripheral rim flange 177 and an upper collar 178 of generally larger diameter than a lower portion 179 of the tip 170. The tip 170 is preferably formed from conductive polypropylene. When the tip 170 is inserted into an orifice of a holding structure 176, the flange 177 contacts the top of structure 176 and the collar 178 provides a snug but releasable interference fit between the tip 170 and the holding structure 176. Alternatively, each holding structure 176 may be configured to loosely receive a tip 170 so that the tip 170 is more easily removed from the holding structure when engaged by an aspirator tube 860.

An axially extending through-hole 180 passes through the tip 170. Hole 180 includes an outwardly flared end 181 at the top of the tip 170 which facilitates insertion of a tubular probe (not shown) into the tip 170. Two annular ridges 183 may be provided on the inner wall of hole 180. Ridges 183 provide an interference friction fit between the tip 170 and a tubular probe inserted into the tip 170.

The bottom end of the tip 170 preferably includes a beveled portion 182. When tip 170 is used on the end of an aspirator tube 860 that is inserted to the bottom of a reaction receptacle, such as a receptacle 162 of an MRD 160, the beveled portion 182 prevents a vacuum from forming between the end of the tip 170 and the bottom of the reaction receptacle.

Further details regarding the MRD 160 may be found in U.S. Pat. No. 6,086,827.

Specimen Preparation Procedure

For nucleic acid tests, it may be necessary to lyse or permeabilize cells to first release a targeted nucleic acid and make it available for hybridization with a detection probe. See, e.g., Clark et al., "Method for Extracting Nucleic Acids from a Wide Range of Organisms," U.S. Pat. No. 5,786,208. If the cells are lysed, the contents of the resulting lysate may include, in addition to nucleic acids, organelles, proteins (including enzymes such as proteases and nucleases), carbohydrates, and lipids, which may necessitate further purification of the nucleic acids. Additionally, for pathogenic organisms, chemical or thermal inactivation of the organisms may be desirable. Cells may be lysed or permeabilized by a variety of means well known to those skilled in the art, including by chemical, mechanical (e.g., sonication) and/or thermal means.

Various methods for capturing nucleic acids using magnetically-responsive solid supports are known in the art and can be employed in the present invention. These methods may be specific or non-specific for the targeted nucleic acid. One such method is Solid Phase Reversible Immobilization, which is based on the selective immobilization of nucleic acids onto magnetic microsolid support having carboxyl group-coated surfaces. See U.S. Pat. No. 5,705,628. In another method, magnetic particles having poly(dT) sequences derivatized thereon bind to capture probes having 5' poly(dA) tails and 3' target binding sequences. See U.S. Pat. No. 6,534,273. Still another approach is based on the ChargeSwitch® Technology, which is a magnetic bead-based technology that provides a switchable surface that is charge dependent on the surrounding buffer pH to facilitate nucleic acid purification (Invitrogen Corporation, Carlsbad, Calif.; Cat. No. CS12000). In low pH conditions, the ChargeSwitch® Magnetic Beads have a positive charge that binds the negatively charged nucleic acid backbone. Proteins and other contaminants that are not bound can be washed away. By raising the pH to 8.5, the charge on the surface is neutralized and the bound nucleic acids are eluted.

For approaches involving capture probes, the capture probes may be specific or non-specific for the targeted nucleic acids. A specific capture probe includes a target binding region that is selected to bind to a target nucleic acid under a predetermined set of conditions and not to non-target nucleic acids. A non-specific capture probe does not discriminate between target and non-target nucleic acids under the conditions of use. Wobble capture probes are an example of a non-specific capture probe and may include at least one random or non-random poly(K) sequence, where "K" can represent a guanine, thymine or uracil base. See U.S. Patent Application Publication No. US 2008-0286775 A1. In addition to hydrogen bonding with cytosine, its pyrimidine complement, guanine will also hydrogen bond with thymine and uracil. Each "K" may also represent a degenerate nucleoside such as inosine or nebularine, a universal base such as 3-nitropyrrole, 5-nitroindole or 4-methylindone, or a pyrimidine or purine base analog such as dP or dK. The poly(K) sequence of a wobble capture probe is of sufficient length to non-specifically bind the target nucleic acid, and is preferably 6 to 25 bases in length.

Sample material is prepared for a magnetic separation procedure by dispensing a specified amount of a target capture reagent into each sample-holding receptacle of a receptacle device. Dispensing may be performed manually or by an automated, robotic pipetting apparatus—into each of the receptacles 162 of the MRD 160. The target capture reagent includes a solid support material able to directly or indirectly bind to an analyte, such as through a capture probe, thereby immobilizing the analyte on the solid support comprises magnetically-responsive particles or beads. The amount dispensed into each receptacle 162 is typically in the range of 100-500 μL.

Magnetic Separation Stations

Figure 5:
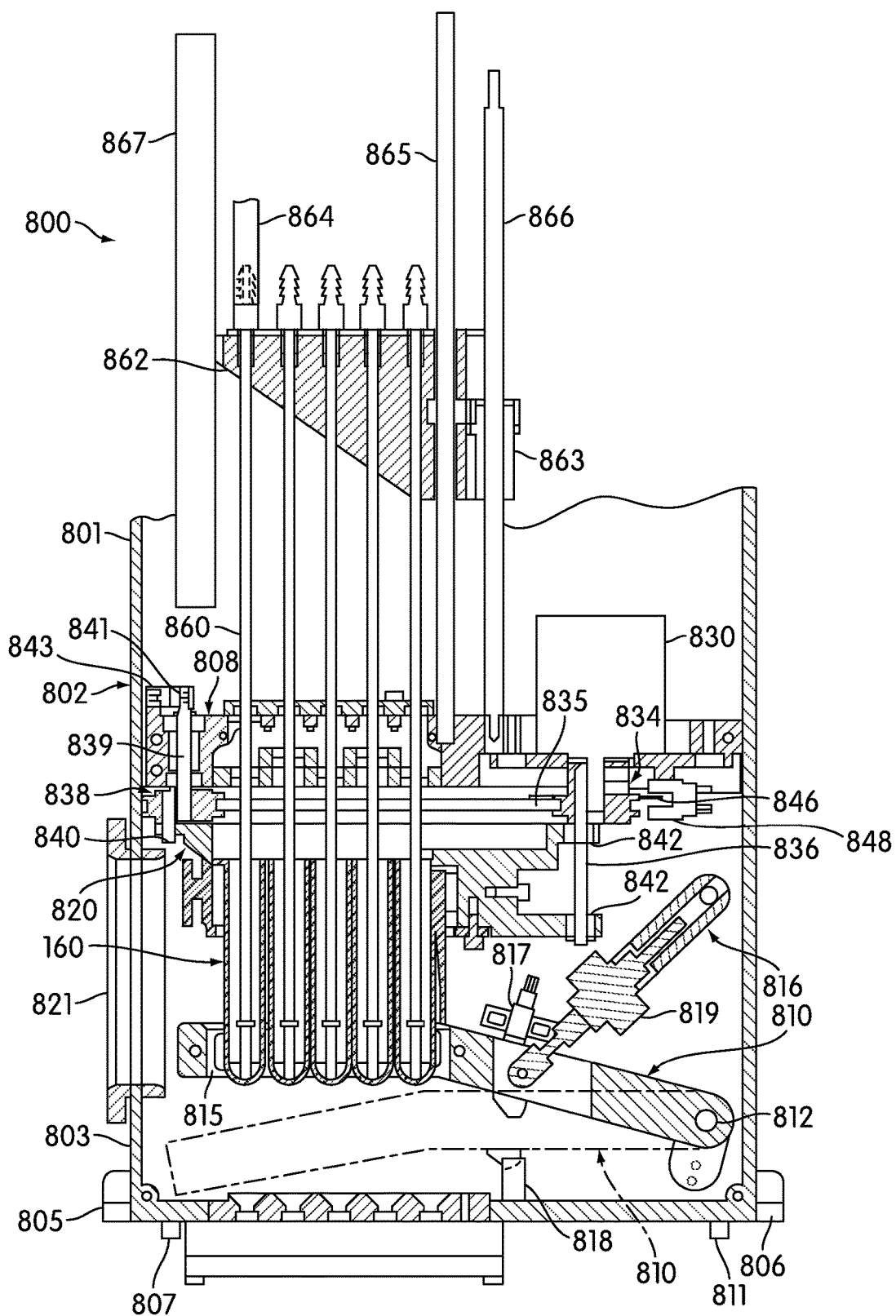
FIG. 5 is a partial transverse cross-section of the magnetic separation station.

Turning to FIGS. 4-5, a magnetic separation station 800 includes a module housing 802 having an upper section 801 and a lower section 803. Mounting flanges 805, 806 extend from the lower section 803 for mounting the magnetic separation station 800 to a support surface by means of suitable mechanical fasteners. Locator pins 807 and 811 extend from the bottom of lower section 803 of housing 802. Pins 807 and 811 register with apertures (not shown) formed in the support surface to help to locate the magnetic separation station 800 on the support surface before the housing 802 is secured by fasteners.

A loading slot 804 extends through the front wall of the lower section 803 to allow a transport mechanism (not shown) to place a receptacle device, such as an MRD 160, into and remove the receptacle device from the magnetic separation station 800. A tapered slot extension 821 may be provided around a portion of the loading slot 804 to facilitate receptacle insertion through the slot 804. A divider 808 separates the upper section 801 from the lower section 803.

Figure 7:
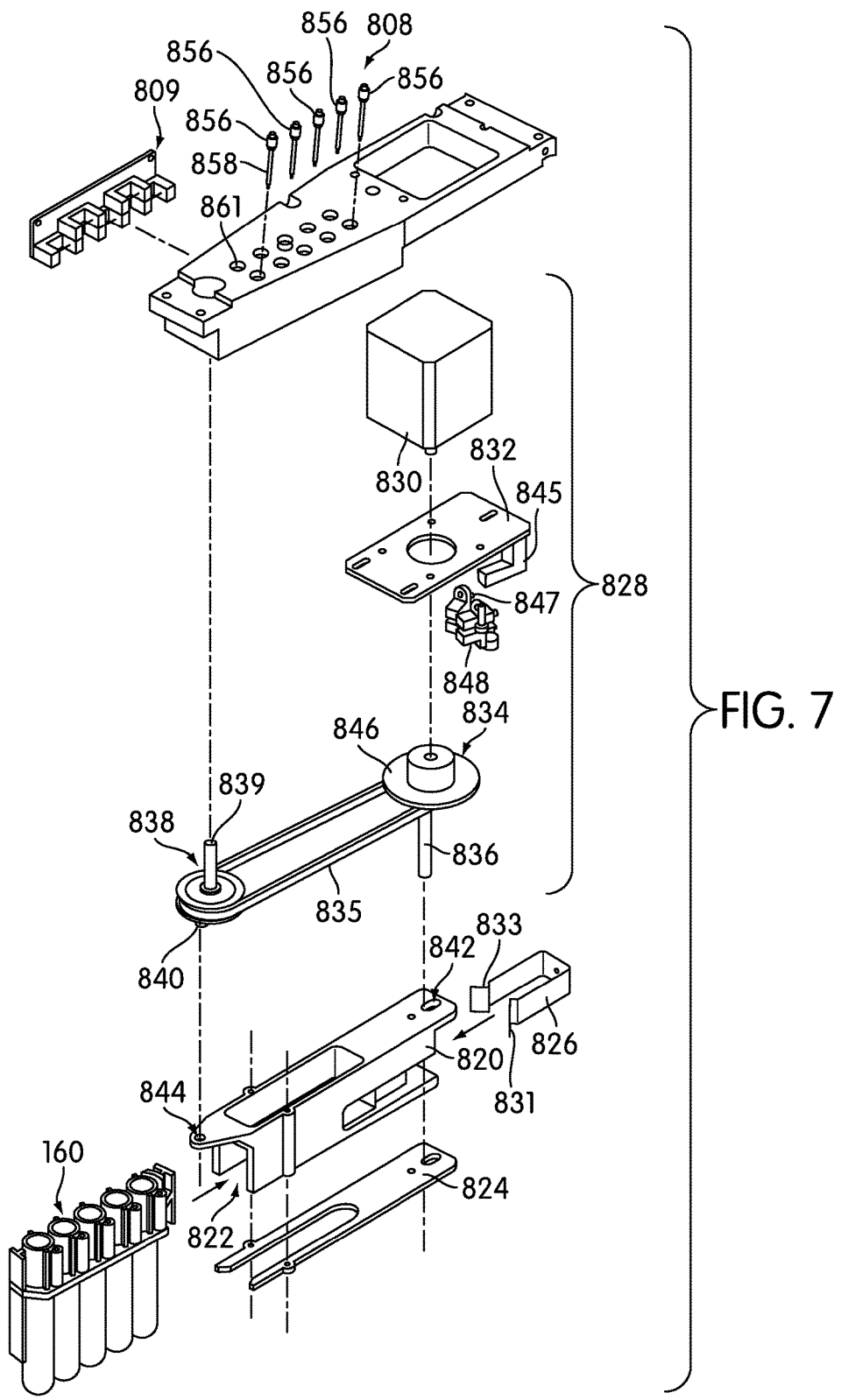
FIG. 7 is an exploded perspective view of a receptacle carrier unit, an orbital mixer assembly, and a divider plate of the magnetic separation station.

A receptacle carrier unit 820 is disposed adjacent the loading slot 804, below the divider 808, for operatively supporting the receptacle disposed within the magnetic separation station 800. For purposes of illustration, the receptacle carrier unit 820 is shown in FIG. 5 carrying an MRD 160, but other receptacles, including single, individual receptacles and multiple receptacle devices having receptacles of varying shapes and sizes, may be used. Turning to FIG. 7, the receptacle carrier unit 820 has a slot 822 for receiving the upper end of a receptacle device, such as an MRD 160. In the illustrated embodiment, a lower fork plate 824 attaches to the bottom of the receptacle carrier unit 820 and supports the underside of the connecting rib structure 164 of the MRD 160 when slid into the carrier unit 820 (see FIGS. 8 and 9). A spring clip 826 is attached to the carrier unit 820 with its opposed prongs 831, 833 extending into the slot 822 to releasably hold the receptacle within the carrier unit 820.

As an alternative to the arrangement shown in FIG. 7, the receptacle carrier unit 820 may comprise a single, injection molded part, which may include an integrally-formed ledge if configured for supporting an MRD 160, and an integrally-formed plastic spring element for retaining a receptacle within the receptacle carrier unit 820.

An orbital mixer assembly 828 is coupled to the carrier unit 820 for orbitally mixing the contents of an MRD, or other receptacle device, held by the receptacle carrier unit 820. The orbital mixer assembly 828 includes a stepper motor 830 mounted on a motor mounting plate 832, a drive pulley 834 having an eccentric pin 836, an idler pulley 838 having an eccentric pin 840, and a belt 835 connecting drive pulley 834 with idler pulley 838. A suitable stepper motor includes a VEXTA, model number PK245-02A, available from Oriental Motors Ltd. of Tokyo, Japan, and suitable belts 835 include a timing belt, model number A 6G16-170012, available from SDP/SI of New Hyde Park, N.Y. As shown in FIGS. 5 and 7, eccentric pin 836 fits within a slot 842 formed longitudinally in the receptacle carrier unit 820. Eccentric pin 840 fits within a circular aperture 844 formed in the opposite end of receptacle carrier unit 820. As the motor 830 turns the drive pulley 834, idler pulley 838 also rotates via belt 835 and the receptacle carrier unit 820 is moved in a horizontal orbital path by the eccentric pins 836, 840 engaged with the apertures 842, 844, respectively, formed in the carrier unit 820. The rotation shaft 839 of the idler pulley 838 preferably extends upwardly and has a transverse slot 841 formed therethrough. An optical slotted sensor 843 is disposed at the same level as the slot 841 and measures the frequency of the idler pulley 838 via the sensor beam intermittently directed through slot 841 as the shaft 839 rotates. A suitable sensor includes an Optek Technology, Inc., model number OPB980T11, sensor, available from Optek Technology, Inc. of Carrollton, Tex.

As an alternative to slot 841 and sensor 843, the frequency of idler pulley 838 may be measured by means of an encoder (not shown) mounted on the top of shaft 839.

Drive pulley 834 also includes a locator plate 846. Locator plate 846 passes through slotted optical sensors 847, 848 mounted to a sensor mounting bracket 845 extending from motor mounting plate 832. Suitable sensors include Optek Technology, Inc., model number OPB980T11, sensors, available from Optek Technology, Inc. of Carrollton, Tex. Locator plate 846 has a plurality of circumferentially spaced axial openings formed therein which register with one or both sensors 847, 848 to indicate a position of the orbital mixer assembly 828, and thus a position of the receptacle carrier unit 820.

As an alternative to locator plate and sensors 847, 848, the frequency and position of drive pulley 834 may be measured by means of an encoder (not shown) coupled to the pulley 834.

A pivoting magnet moving apparatus 810 is attached inside the lower section 803 so as to be pivotable about point 812. The magnet moving apparatus 810 carries permanent magnets 814, which are positioned on either side of a slot 815 formed in the magnet moving apparatus 810. The magnet moving apparatus 810 is constructed and arranged to move the magnets 814 between an operational position and a non-operational position with respect to a receptacle device carried in the receptacle carrier unit 820. In the operational position, the magnets 814 are disposed adjacent the receptacle, e.g., the MRD 160, and in sufficient proximity to the receptacle so that magnetically-responsive solid supports within each receptacle 162 are drawn out of suspension by the attraction of the magnetic fields of the magnets 814. In the non-operational position, the magnets are disposed at a sufficient distance from the receptacles 162 so as to have no substantial effect on the contents of the receptacles 162. In the present context, "no substantial effect" means that the magnetically-responsive solid supports are not drawn out of suspension by the attraction of the magnetic fields of the magnets 814.

Preferably five magnets, one corresponding to each individual receptacle 162 of the MRD 160, are held in an aligned arrangement on each side of the magnet moving apparatus 810. The magnets are preferably made of neodymium-iron-boron (NdFeB), minimum grade n-35 and have preferred dimensions of 0.5 inch width, 0.3 inch height, and 0.3 inch depth. An electric actuator, generally represented at 816, pivots the magnet moving apparatus 810 up and down, thereby moving the magnets 814. As shown in FIG. 5, actuator 816 preferably comprises a rotary stepper motor 819 which rotates a drive screw mechanism coupled to the magnet moving apparatus 810 to selectively raise and lower the magnet moving apparatus 810. Motor 819 is preferably an HSI linear stepper actuator, model number 26841-05, available from Haydon Switch and Instrument, Inc. of Waterbury, Conn.

A sensor 818, preferably an optical slotted sensor, is positioned inside the lower section 803 of the housing for indicating the down, or "home", or non-operational, position of the magnet moving apparatus 810. Another sensor 817, also preferably an optical slotted sensor, is preferably provided to indicate the up, or operational, position of the magnet moving apparatus 810. Suitable sensors include model number OPB980T11, available from Optek Technology, Inc. of Carrollton, Tex.

Figure 10:
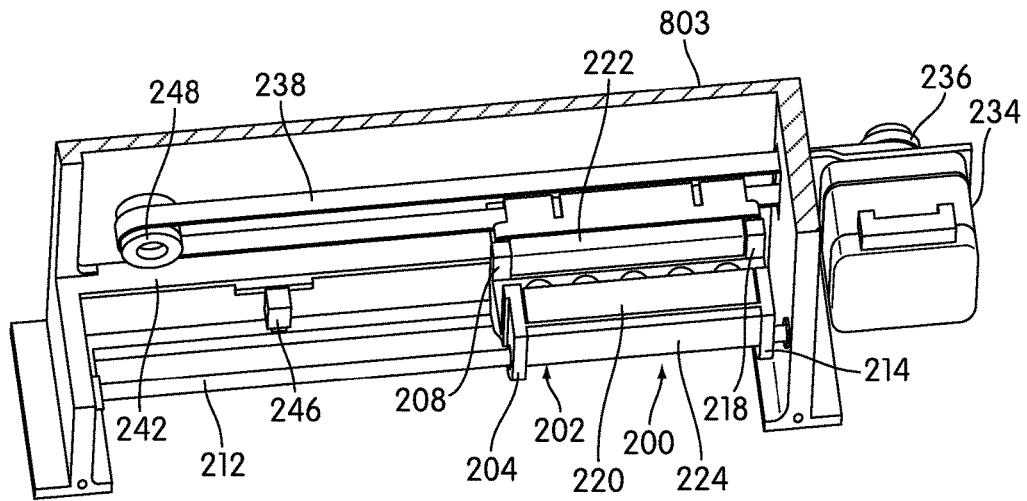
FIG. 10 is a top perspective view of a portion of a magnetic separation station illustrating an alternate embodiment of a magnet moving apparatus.
Figure 11:
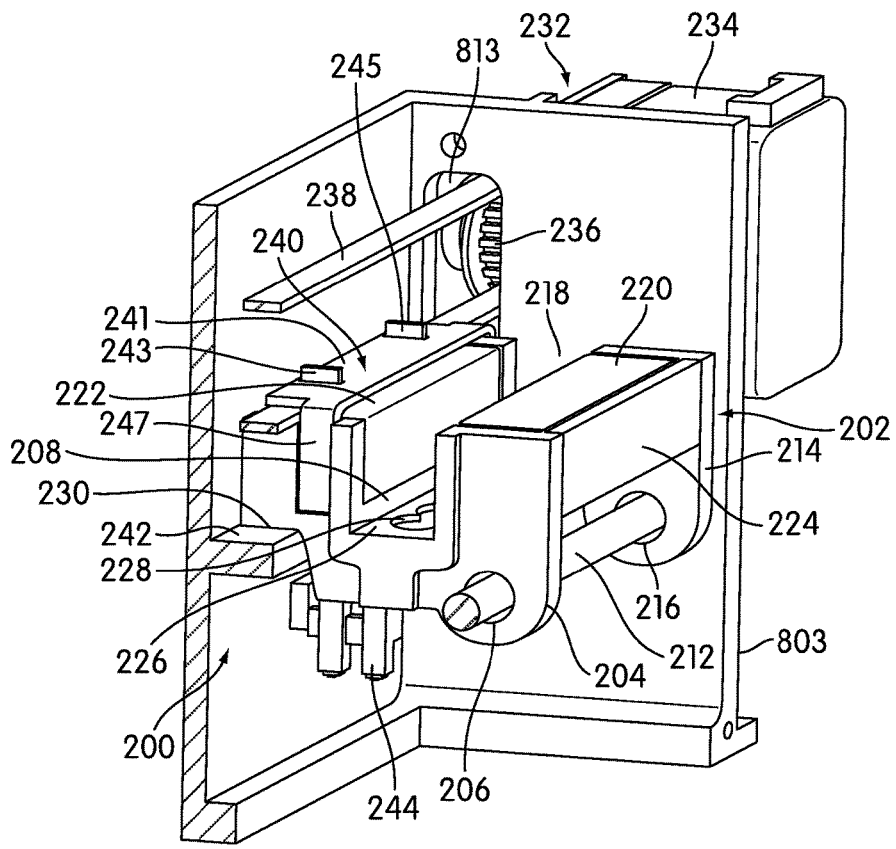
FIG. 11 is a partial perspective view the magnet moving apparatus of FIG. 10.

An alternate embodiment of a magnet moving apparatus for moving the magnets between operational and non-operational positions with respect to the receptacle is shown in FIGS. 10 and 11. The magnet moving apparatus comprises magnet slide 200 which comprises a magnet sled 202 that is moved along a linear path by a drive system 232.

More specifically, the magnet sled 202 includes a first wall 204 having a guide rod aperture 206 and a rectangular, U-shaped cutout 208. The a magnet sled 202 further comprises a second wall 214 having a guide rod aperture 216 and a rectangular cutout 218 formed therein. A first magnet 220 is positioned between the first wall 204 and the second wall 214 on one side of the respective cutouts 208, 218 and is supported by a first magnet backing plate 224. Similarly, a second magnet 222 is disposed between the first wall 204 and the second wall 214 on an opposite side of the respective rectangular cutouts 208, 218 and is backed by a magnet backing plate (not shown). Magnets 220, 222 may be made from NdFeB, grade n-35 or grade n-40. As an alternative to single magnets 220, 222 on opposite sides of the magnet sled 202, individual magnets may be provided on each side of the sled 202, one for each receptacle 162. In one embodiment, the sled includes five magnets on each side, each magnet having a size of approximately 12 mm×12 mm×7.5 mm and being made from NdFeB, grade n-40. The number of magnets corresponds to the number of receptacles 162 comprising the MRD 160.

Magnet sled 202 further includes a bottom plate 226 with a plurality of tip stripping elements in the form of stripping openings 228 formed therein. Operation of the tip stripping openings 228 will be described below. Finally, the magnet sled 202 includes a guide surface formed in part by a straight laterally extended edge 230 formed in the first wall 204. A similar laterally extending straight edge is formed in the back wall 214. Any of the first and second walls 204, 214, first and second magnet backing plates 224, and bottom plate 226 may be integrally formed with each other. Suitable materials for the first and second walls 204, 214 and bottom plate 226 include non-magnetically-responsive materials such as plastics and aluminum. Preferred material for the first and second magnet backing plates 224 include magnetically-responsive materials, such as steel, to increase magnetic flux flowing through the magnets.

The drive system 232 comprises a drive motor 234 having a drive pulley 236 and mounted on the outside of the lower housing 803. A drive belt 238 is carried on the drive pulley 236 and an idler pulley 248 and extends through an opening 813 formed in the lower housing 803. Opposite ends 243, 245 of the drive belt 238 are attached to the magnet sled 202 by means of a coupling bracket 240. Suitable belts are available from the Gates Corporation.

The coupling bracket 240 includes a top plate 241 disposed across the top of the second magnet 222 and having belt retaining slots within which opposite ends 243, 245 of the drive belt 238 are inserted and secured. A retainer tab 247 bent transversely with respect to the top plate 241 is positioned within a conforming slot formed in the first wall 204. A similar tab (not shown) is provided on the opposite end of the top plate 241 and extends within a conforming slot formed in the second wall 214 for securing the coupling bracket 240 to the magnet sled 202.

The magnet sled 202 is disposed inside the lower housing 803 with the guide surface 230 supported on a guide ledge 242 extending along an inner surface of the lower housing 803. The opposite side of the magnet sled 202 is supported by a guide rod 212 extending across the lower housing 803 and through the guide rod apertures 206 and 216. A bushing (not shown) may be provided at either or both of the guide rod apertures 206, 216 for securely and slidably supporting the magnet sled 202.

Rotation of the drive pulley 236 by the drive motor 234 turns the drive belt 238 to thereby move the magnet sled 202 between a non-operational position, such as shown in FIGS. 10 and 11, and an operational position whereby the magnet sled 202 is moved to the opposite side of the lower housing 803. When the magnet sled 202 is moved to the operational position, the lower ends of the receptacles 162 pass through the rectangular cutouts 208, 218 of the first wall 204 and second wall 214, respectively, so as to be disposed between the first magnet 220 and the second magnet 222.

A retracted position sensor 244 mounted to an inner surface of the lower housing 803 indicates when the magnet sled 202 is in a retracted, or non-operational, position. Similarly, an extended position sensor 246, also mounted to an inner surface of the lower housing 803, indicates when the magnet sled 202 is in an extended, or operational, position. Sensors 244 and 246 may comprise slotted optical sensors which detect the presence of a tab (not shown) projecting from a lower portion of the magnet slide 202.

Figure 12:
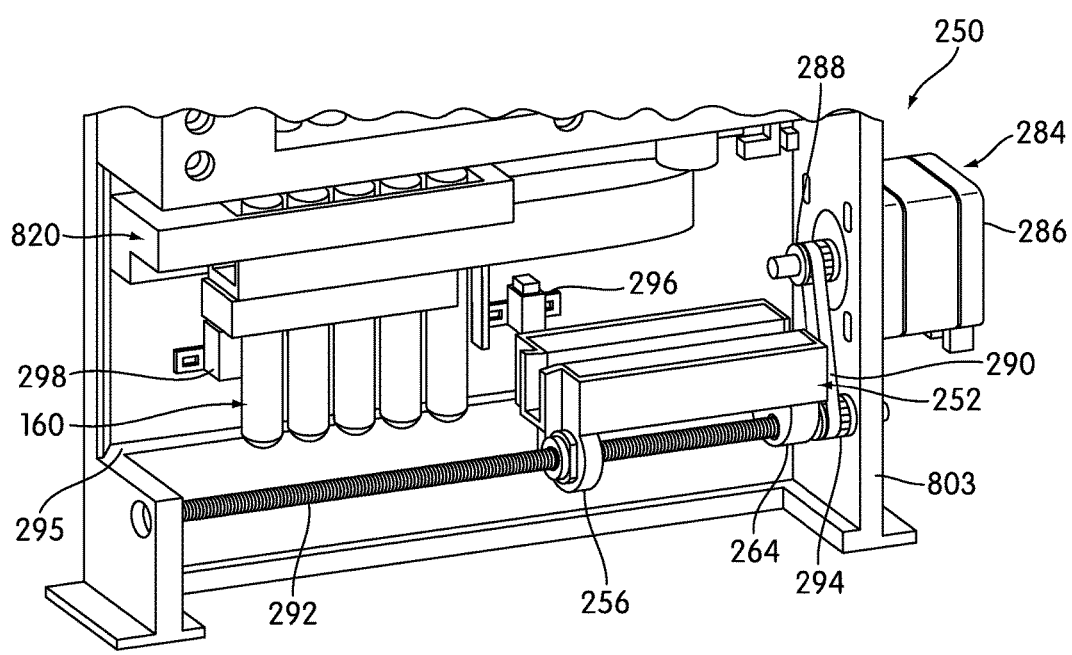
FIG. 12 is a partial perspective view of a magnetic separation station illustrating a further alternate embodiment of a magnet moving apparatus.
Figure 13:
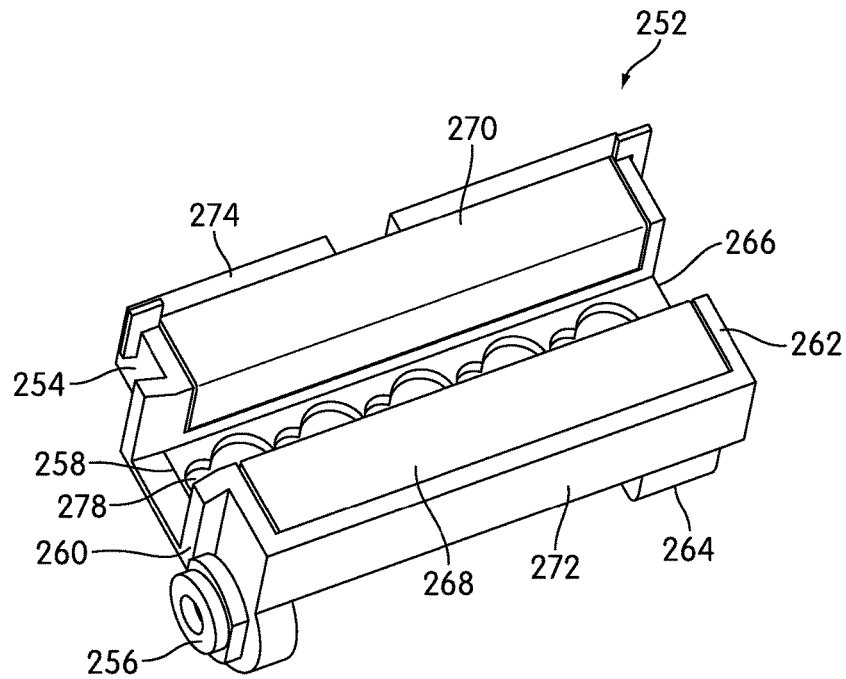
FIG. 13 is a top perspective view of a magnet sled of the magnet moving apparatus of FIG. 12.
Figure 14:
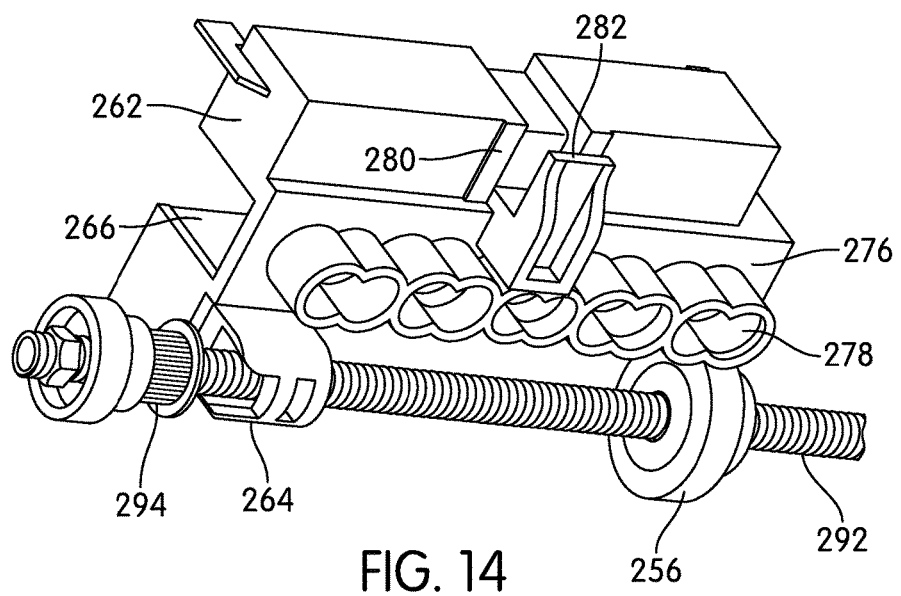
FIG. 14 is a bottom perspective view of the magnet sled of FIG. 13.

A further alternative embodiment of a magnet moving apparatus is shown in FIGS. 12-15. The magnet moving apparatus of FIGS. 12-15 comprises a magnet slide 250 including a magnet sled 252 and a drive system 284 which moves the magnet sled 252 between a non-operational position (as shown in FIG. 12) and an operational position with respect to an receptacle.

More specifically, the magnet sled 252 comprises a first wall 254 including a screw follower 256 and a rectangular opening 258. An extended flange 260 may be provided around the rectangular opening 258. The magnet sled 252 further comprises a second wall 262 having a guide bushing 264 and a rectangular opening 266. A first magnet 268 is disposed between the first wall 254 and the second wall 262 and is supported by a first magnet backing plate 272. Similarly, a second magnet 270 is disposed between the first wall 254 and the second wall 262 on an opposite side of the rectangular openings 258, 266 and is supported by a second magnet backing plate 274. Again, as an alternative to single magnets 268, 270 on opposite sides of the magnet sled 252, five individual magnets having a size of approximately 12 mm×12 mm×8 mm and made from NdFeB, grade n-40 can be provided on each side of the sled 252.

The magnet sled 252 further includes a bottom plate 276 in which a plurality of tip stripping openings 278 are formed, a guide surface 280, and a retainer bracket 282. Guide surface 280 may comprise two surfaces disposed on opposite sides of the retainer bracket 282.

A drive system 284 includes a drive motor to a 286 mounted on the exterior of the lower housing 803 and having a drive pulley 288. A threaded drive screw 292 extends across the lower housing 803 and is journaled at its opposite ends to the lower housing wall so as to be rotatable about its longitudinal axis. Threaded drive screw 292 further includes a pulley 294 located at one end thereof. The threaded drive screw 292 is operatively coupled to the drive motor 286 by means of a drive belt 290 carried on the drive pulley 288 of the drive motor 286 and the pulley 294 of the threaded drive screw 292.

The threaded drive screw 292 extends through the screw follower 256 of the first wall 254 and the guide bushing 264 of the second wall 262. The guide surface 280 on the bottom surface of the magnet sled 252 and located on the opposite side of the sled 252 from the screw follower 256 and guide bushing 264 slidably rests on a guide flange 295 extending along an inner wall of the lower housing 803. A lower portion of the retainer bracket 282 extends beneath the guide flange 295 so that the guide flange is disposed between the guide surface 280 and the retainer bracket 282.

Rotation of the drive pulley 288 by the drive motor 286 is transferred to the threaded drive screw 292 by means of the drive belt 290. The rotating drive screw 292 engaged with the screw follower 256 causes linear translation of the magnet sled 252 in a longitudinal direction with respect to the drive screw 292. Rotation of the drive screw 292 in one direction will cause left to right translation of the magnet sled 252, and rotation of the screw 292 in the opposite direction will cause right to left translation of the magnet sled 252. The retainer bracket 282 engaged with the underside of the guide flange 295 prevents the magnet sled 252 from tipping out of contact with the guide flange 295 due to friction between the drive screw 292 and the screw follower 256.

When the magnet sled 252 is moved from the non-operational position, shown in FIG. 12, to an operational position, the receptacle passes through the rectangular openings 258, 266 and is disposed between the first magnet 268 and second magnet 270. The extended flange 260 formed around the rectangular opening 258 of the first wall 254 will assist in guiding the receptacle through the opening 258.

A retracted position sensor 296 mounted to the inner wall of the lower housing 803 indicates when the magnet sled 252 is in a retracted, or non-operational, position, and an extended position sensor 298, also mounted to the inner wall of the lower housing 803, indicates when the magnet sled 252 is in an extended, or operational, position with respect to the receptacle. Sensors 296 and 298 may comprise optical sensors which detect the presence of a tab extending from a portion of the magnet sled 252.

Returning to FIG. 4, wash solution delivery tubes 854 connect to fittings 856 and extend through a top surface of the module housing 802. Wash solution delivery tubes 854 extend through the divider 808 via fittings 856, to form a wash solution delivery network.

Figure 8:
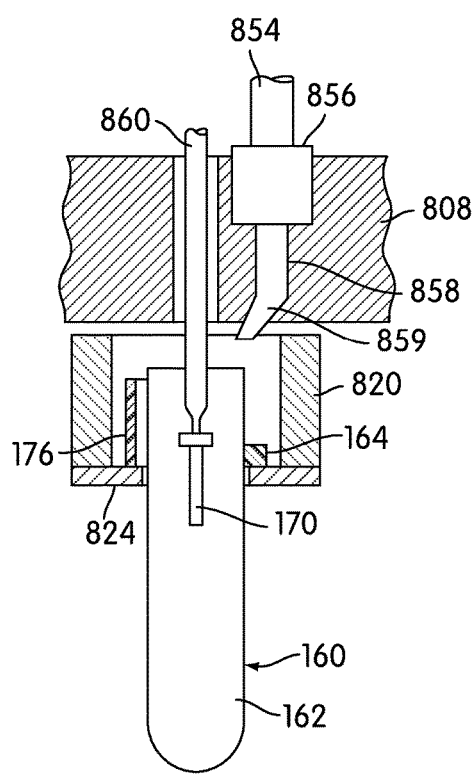
FIG. 8 is a partial cross-sectional view of a wash solution dispenser nozzle, an aspirator tube with a contamination-limiting tip engaged with an end thereof, and a receptacle carrier unit of the magnetic separation station, showing a multiple receptacle device reaction receptacle carried in the receptacle carrier unit and the aspirator tube and contamination-limiting tip inserted into a receptacle of the multiple receptacle device.
Figure 9:
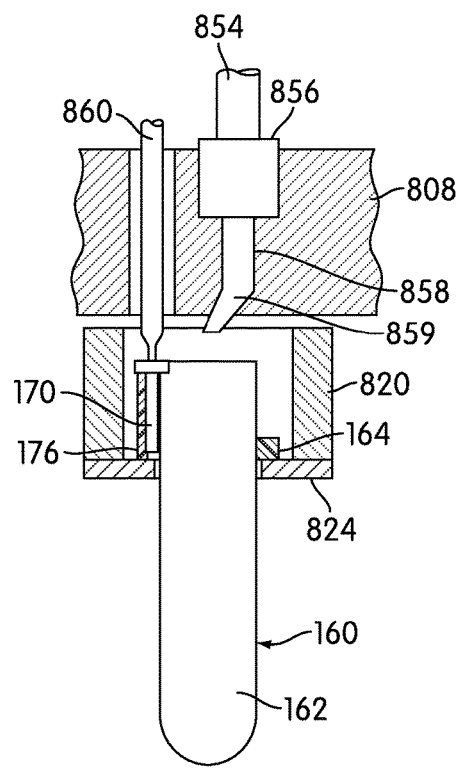
FIG. 9 is a partial cross-sectional view of the wash solution dispenser nozzle, the aspirator tube, and the receptacle carrier unit of the magnetic separation station, showing the multiple receptacle device carried in the receptacle carrier unit and the aspirator tube engaging the contamination-limiting tip held in a contamination-limiting element holding structure of the multiple receptacle device.

As shown in FIGS. 8 and 9, wash solution dispenser nozzles 858 extending from the fittings 856 are disposed within the divider 808. Each nozzle is located above a respective receptacle 162 of the MRD 160 at a laterally off-center position with respect to the receptacle 162. Each nozzle includes a laterally-directed lower portion 859 for directing the wash solution into the respective receptacle 162 from the off-center position. Suitable wash solutions are known to those skilled in the art, an example of which contains 10 mM Trizma base, 0.15 M LiCl, 1 mM EDTA, and 3.67 mM lithium lauryl sulfate (LLS), at pH 7.5. Dispensing fluids into the receptacles 162 in a direction having a lateral component can limit splashing as the fluid runs down the sides of the respective receptacles 162. In addition, the laterally directed fluid can rinse away materials clinging to the sides of the respective receptacles 162.

As shown in FIGS. 4 and 5, aspirator tubes 860, or probes, extend through a tube holder 862, to which the tubes 860 are fixedly secured, and extend through openings 861 in the divider 808. A tip sense printed circuit board ("PCB") 809 (see FIG. 7) is attached by mechanical fasteners to the side of divider 808, below openings 861. Aspirator hoses 864 connected to the aspirator tubes 860 extend to a vacuum pump (not shown), with aspirated fluid drawn off into a fluid waste container carried (not shown). In one embodiment, each of the aspirator tubes 860 has a length of 12 inches with an inside diameter of 0.041 inches.

The tube holder 862 is attached to a drive screw 866 actuated by a lift motor 868. A suitable lift motor includes the VEXTA, model number PK245-02A, available from Oriental Motors Ltd. of Tokyo, Japan, and a suitable drive screw includes the ZBX series threaded anti-backlash lead screw, available from Kerk Motion Products, Inc. of Hollis, N.H. In the illustrated embodiment, the tube holder 862 is attached to a threaded sleeve 863 of the drive screw 866. Rod 865 and slide rail 867 function as a guide for the tube holder 862. Alternatively, a linear bearing (not shown) may be employed as a guide for the tube holder 862. Z-axis sensors 829, 827 (slotted optical sensors) cooperate with a tab extending from the tube holder 862 and/or the threaded sleeve 863 to indicate top and bottom of stroke positions of the aspirator tubes 860. Suitable Z-axis sensors include Optek Technology, Inc., model number OPB980T11, sensors, available from Optek Technology, Inc. of Carrollton, Tex. Together, the tube holder 862, lift motor 868, and drive screw 866 comprising an embodiment of a moving mechanism for the tubes 860.

Cables bring power and control signals to the magnetic separation station 800, via one or more connectors (one such connector is shown at reference number 870).

The magnet moving apparatus 810, 200, 250 is initially in a non-operational position (e.g., as shown in phantom in FIG. 5 and in FIGS. 10 and 12), as verified by the retracted position sensor 818, 244, 296, when the receptacle is inserted into the magnetic separation station 800 through the insert opening 804 and into the receptacle carrier unit 820. When the magnet moving apparatus is in the non-operational position, the magnetic fields of the magnets will have no substantial effect on the magnetically-responsive solid supports contained in the receptacle. The orbital mixer assembly 828 moves the receptacle carrier unit 820 a portion of a complete orbit so as to move the receptacle carrier unit 820 and MRD 160 laterally, so that each of the tips 170 carried by the tip holding structures 176 of the MRD 160 is aligned with each of the aspiration tubes 860, as shown in FIG. 9. The position of the receptacle carrier unit 820 is verified, for example, by the locator plate 846 and one of the sensors 847, 848. Alternatively, the stepper motor 830 can be moved a known number of steps to place the receptacle carrier unit 820 in the desired position, and one of the sensors 847, 848 can be omitted. Note that magnet moving apparatus cannot move to an operational position when the receptacle carrier unit 820 has been moved to this tip engagement position because the MRD 160 carried by unit 820 will interfere with movement of the magnet moving apparatus.

The tube holder 862 and aspirator tubes 860 are lowered by the lift motor 868 and drive screw 866 until each of the aspirator tubes 860 frictionally engages a conduit, e.g., a tip 170, held in an associated carrying structure 176 on the MRD 160.

Figure 6:
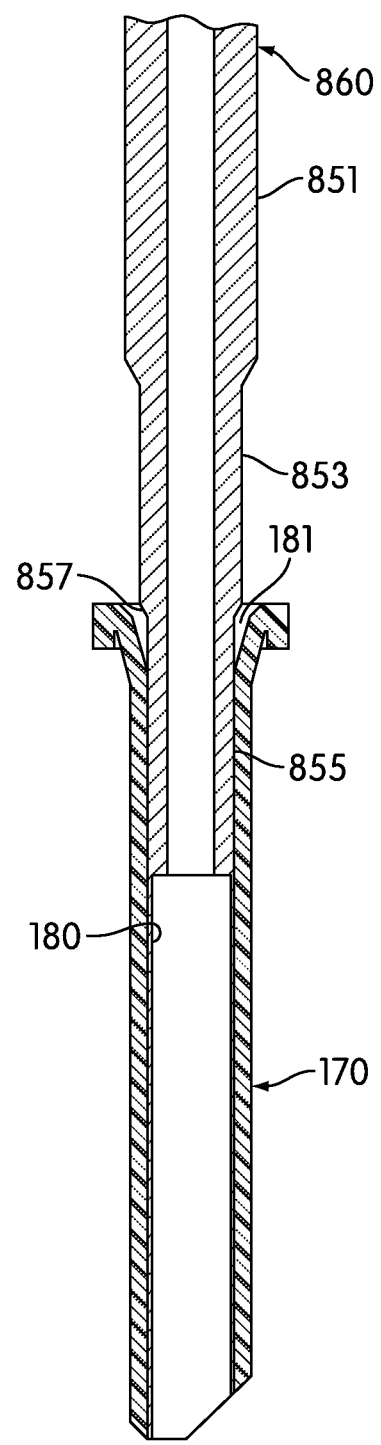
FIG. 6 is a partial transverse cross-section of a tip of an aspirator tube of the magnetic separation station with a contamination-limiting tip carried on the end thereof.

As shown in FIG. 6, the lower end of each aspirator tube 860 is characterized by a tapering, step construction, whereby the tube 860 has a first portion 851 along most of the extent of the tube, a second portion 853 having a diameter smaller than that of the first portion 851, and a third portion 855 having a diameter smaller than that of the second portion 853. The diameter of the third portion 855 is such as to permit the end of the tube 860 to be inserted into the flared portion 181 of the through-hole 180 of the tip 170 and to create an interference friction fit between the outer surface of third portion 855 and a portion of the inner wall of the through-hole 180, such as the two annular ridges 183 (see FIG. 2) or alternatively, longitudinally-oriented ridges (not shown), that line the inner wall of hole 180 of tip 170. An annular shoulder 857 is defined at the transition between second portion 853 and third portion 855. The shoulder 857 limits the extent to which the tube 860 can be inserted into the tip 170, so that the tip can be stripped off after use, as will be described below.

The tips 170 may be at least partially electrically conductive, so that the presence of a tip 170 on an aspirator tube 860 can be verified by the capacitance of a capacitor comprising the aspirator tubes 860 and tips 170 as one half of the capacitor and the surrounding hardware of the magnetic separation station 800 (e.g., the metal divider 808) as the other half of the capacitor. A suitable resin for forming the tips 170 is available from Fiberfil® Engineered Plastics Inc. as product number PP-61/EC/P BK, which is a carbon filled conductive polypropylene. As determined by the tip sense PCB 809, the capacitance will change when the tips 170 are engaged with the ends of the aspirator tubes 860.

In addition to, or as an alternative to capacitive tip sensing, five optical slotted sensors (not shown) can be strategically positioned above the divider 808 to verify the presence of a tip 170 on the end of each aspirator tube 860. Suitable "tip-present" sensors include Optek Technology, Inc., model number OPB930W51, sensors, available from Optek Technology, Inc. of Carrollton, Tex. A tip 170 on the end of an aspirator tube 860 will break the beam of an associated sensor to verify presence of the tip 170. If, following a tip pick-up move, tip engagement is not verified by the tip present sensors for all five aspirator tubes 860, an error signal will be generated. The MRD 160 may be aborted, and the aborted MRD 160 will be retrieved from the magnetic separation station 800 and ultimately discarded, or processing may continue in the receptacle(s) 162 corresponding to aspirator tube(s) 860 for which tip presence is successfully verified After successful conduit engagement, the orbital mixer assembly 828 moves the receptacle carrier unit 820 back to a fluid transfer position shown in FIG. 8 as verified by the locator plate 846 and one or both of the sensors 847, 848.

The magnet moving apparatus 810, 200, 250 is then moved to the operational position (e.g., as shown in FIG. 4) so that the magnets are disposed adjacent opposite sides of the receptacle, such as MRD 160. With the contents of the receptacle subjected to the magnetic fields of the magnets, the magnetically-responsive solid supports having targeted nucleic acids immobilized thereon will be drawn to the sides of the individual receptacles 162 adjacent the magnets. The remaining material within the receptacles 162 should be substantially unaffected, thereby isolating the target nucleic acids. The magnet moving apparatus will remain in the operational position for an appropriate dwell time, as defined by the assay protocol and controlled by the assay manager program, to cause the magnetic solid supports to adhere to the sides of the respective receptacles 162. In one embodiment, the distance between the opposed magnets on opposite sides of the magnet moving apparatus is about 12.4 mm and the diameter of each receptacle 162 of MRD 160 is 11.4 mm, which means there is a gap of 0-1 mm between the magnet and the side of the receptacle 162 when the magnet moving apparatus is in the operational position. When the magnet moving apparatus is moved to the non-operational position, there is a clearance of at least 30 mm between the magnets and the receptacles 160.

The aspirator tubes 860 are then lowered into the receptacles 162 of the MRD 160 to aspirate the fluid contents of the individual receptacles 162, while the magnetic solid supports remain in the receptacles 162, aggregated along the sides thereof, adjacent the magnets. The tips 170 at the ends of the aspirator tubes 860 ensure that the contents of each receptacle 162 do not come into contact with the sides of the aspirator tubes 860 during the aspirating procedure. Because the tips 170 will be discarded before a subsequent MRD 160 is processed in the magnetic separation station 800, the chance of cross-contamination by the aspirator tubes 860 is minimized.

The electrically conductive tips 170 can be used in a known manner for capacitive fluid level sensing within the receptacles 162 of the MRDs 160. The aspirator tubes 860 and the conductive tips 170 comprise one half of a capacitor, the surrounding conductive structure within the magnetic separation station comprises the second half of the capacitor, and the fluid medium between the two halves of the capacitor constitutes the dielectric. Capacitance changes due to a change in the nature of the dielectric can be detected.

The capacitive circuitry of the aspirator tubes 860 can be arranged so that all five aspirator tubes 860 operate as a single gang level-sensing mechanism. When any of the aspirator tubes 860 and its associated tip 170 contacts fluid material within a receptacle 162, capacitance of the system changes due to the change in the dielectric. If the Z-position of the aspirator tubes 860 at which the capacitance change occurs is too high, then a high fluid level in at least one receptacle 162 is indicated, thus implying an aspiration failure or overdispense. On the other hand, if the Z-position of an aspirator tube 860 at which the capacitance change occurs is correct, but one or more of the other tubes has not yet contacted the top of the fluid due to a low fluid level, a low fluid level will be indicated.

Alternatively, the aspirator tube capacitive circuitry can be arranged so that each of the five aspirator tubes 860 operates as an individual level sensing mechanism.

With five individual level sensing mechanisms, the capacitive level sensing circuitry can detect failed fluid aspiration in one or more of the receptacles 162 if the fluid level in one or more of the receptacles 162 is high. Individual capacitive level sensing circuitry can detect failed fluid dispensing into one or more of the receptacles 162 if the fluid level in one or more of the receptacles 162 is low. Furthermore, the capacitive level sensing circuitry can be used for volume verification to determine if the volume in each receptacle 162 is within a prescribed range. Volume verification can be performed by stopping the descent of the aspirator tubes 860 at a position above expected fluid levels, e.g. 110% of expected fluid levels, to make sure none of the receptacles 162 has a level that high, and then stopping the descent of the aspirator tubes 860 at a position below the expected fluid levels, e.g. 90% of expected fluid levels, to make sure that each of the receptacles 162 has a fluid level at least that high.

Following aspiration, the aspirator tubes 860 are raised, the magnet moving apparatus moves to the non-operational position, the receptacle carrier unit 820 is moved to the fluid dispense position (FIG. 9), and a prescribed volume of wash solution is dispensed into each receptacle 162 of the MRD 160 through the wash solution dispenser nozzles 858. To prevent hanging drops of wash solution on the wash solution dispenser nozzles 858, a brief, post-dispensing air aspiration is preferred.

The orbital mixer assembly 828 then moves the receptacle carriers 820 in a horizontal orbital path at high frequency (in one embodiment, 14 HZ, accelerating from 0 to 14 HZ in 1 second) to mix the contents of the receptacle. Mixing by moving, or agitating, the MRD 160 in a horizontal plane is preferred so as to avoid splashing the fluid contents of the receptacle and to avoid the creation of aerosols. Following mixing, the orbital mixer assembly 828 stops the receptacle carrier unit 820 at the fluid transfer position.

To further purify the targeted nucleic acids, the magnet moving apparatus 810, 200, 250 is again moved to the operational position and maintained in the operational position for a prescribed dwell period. After magnetic dwell, the aspirator tubes 860 with the engaged tips 170 are lowered to the bottoms of the receptacles 162 of the MRD 160 to aspirate the test specimen fluid and wash solution in an aspiration procedure essentially the same as that described above.

One or more additional wash cycles, each comprising a dispense, mix, magnetic dwell, and aspirate sequence, may be performed as defined by the assay protocol. Those skilled in the art of NATs will be able to determine the appropriate magnetic dwell times, number of wash cycles, wash solutions, etc. for a desired target capture procedure.

Multiple magnetic separation stations 800 can be employed in an instrument to permit separation wash procedures to be performed on multiple MRDs 160 in parallel. The number of magnetic separation stations 800 will vary depending on the desired throughput of the instrument.

After the final wash step, the magnet moving apparatus 810, 200, 250 is moved to the non-operational position, and the MRD 160 is removed from the magnetic separation station 800 by a transport mechanism. Prior to removing the MRD 160 from the magnetic separation station 800, and preferably prior to magnet retraction, a final residual volume check may be performed by lowering the aspirator tubes 860 and tips 170 to a position just above the bottom of each receptacle 162 to determine if any excess fluid volume remains in the receptacle 162.

After the MRD 160 is removed from the magnetic separation station 800, the tips 170 are stripped from the aspiration tubes 860 by the tip stripping openings 228, 278.

Figure 15:
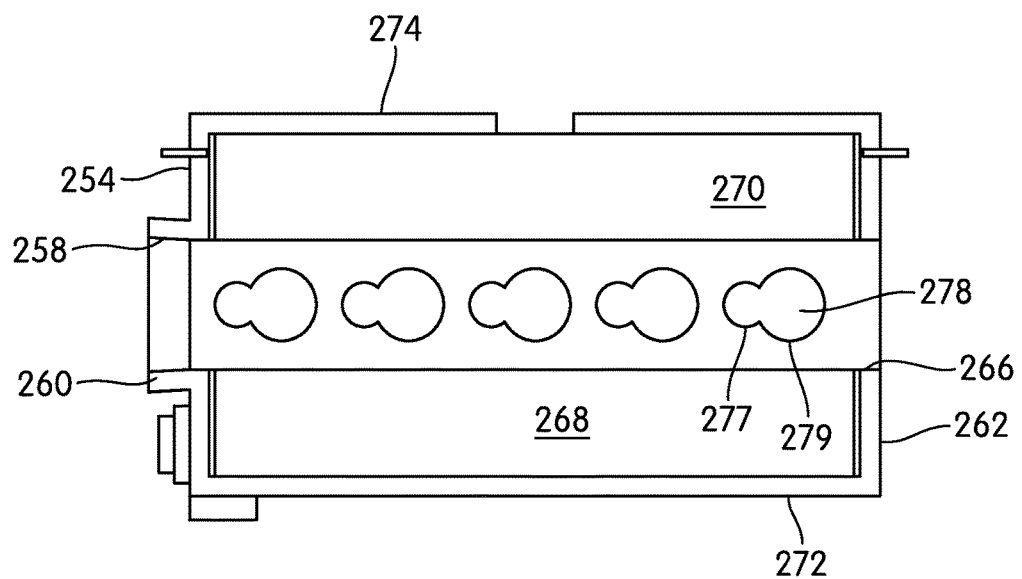
FIG. 15 is a top view of the magnet sled of FIGS. 13 and 14.

The magnet sled 202 of the magnet slide 200 shown in FIG. 10 and the magnet sled 252 of the magnet slide 250 shown in FIG. 12 both include tip stripping openings 228, 278, respectively, formed along a central portion of a lower surface thereof between the first and second magnets. The tip stripping openings, as shown in FIG. 15, comprise keyhole shape openings having a first portion 279 and a second portion 277, with the first portion 279 being larger than the second portion 277. The number of tip stripping openings is equal to the number of aspirator tubes 860, which, in the illustrated embodiment, is five.

To strip the conduits, or tips 170, off of each of the aspirator tubes 860, the magnet sled 202, 252 is positioned beneath the aspirator tubes 860 so that the larger portions 279 of the tip stripping openings 278 are aligned with each of the aspirator tubes 860. The aspirator tubes 860, with the tips 170 disposed thereon, are lowered through the first portions 279 of the stripping openings, which are large enough to permit the tips 170 to pass therethrough. After the tips 170 have passed through the tip stripping openings, the magnet sled is moved slightly so that the aspirator tubes 860 are disposed within the second, smaller portions 277 of the stripping openings, which are large enough to accommodate the aspirator tubes 860, but are smaller than the outside diameter of the rim flange 177 of the tips 170. The aspirator tubes 860 are then raised, and the tips 170 engage the peripheral edges surrounding the second portion 277 of the stripping openings, thereby pulling the tips 170 off of the aspirator tubes 860 as the aspirator tubes 860 ascend. Preferably, the tip stripping openings are disposed at staggered vertical locations so that as the aspirator tubes 860 are raised in unison, the tips 170 encounter the peripheral edges of the stripping openings in a staggered manner. For example, each stripping opening may be at a different vertical position, so that as the aspirator tubes 860 are moved with respect to the stripping openings, the tips 170 are sequentially removed from the associated aspirator tubes 860 one at a time. One benefit of staggering the stripping openings is that it results in smaller forces being exerted on the moving mechanism defined by the tube holder 862, lift motor 868, and drive screw 866.

Although operation of the magnetic separation station 800 was previously described primarily in conjunction with an MRD 160, the inventive aspects of the magnetic separation station 800 is not limited to its use with an MRD 160 as other types of receptacles, including single receptacles and multiple receptacle devices, including receptacles of varying sizes, can be processed in a magnetic separation station embodying aspects of the present invention.

Magnetic Receptacle Holding Stations

Figure 17:
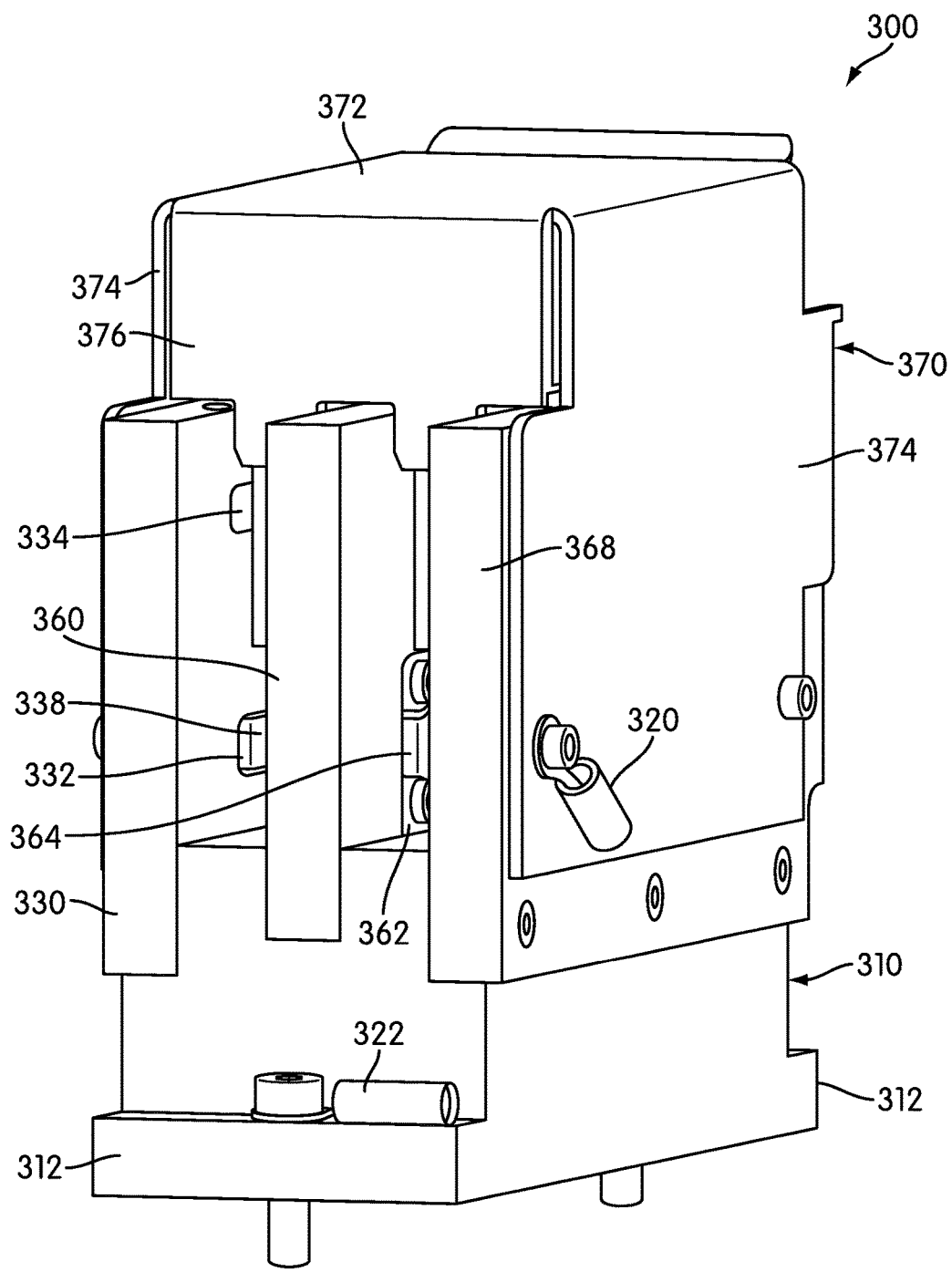
FIG. 17 is a rear perspective view of the magnetic receptacle holding station.
Figure 18:
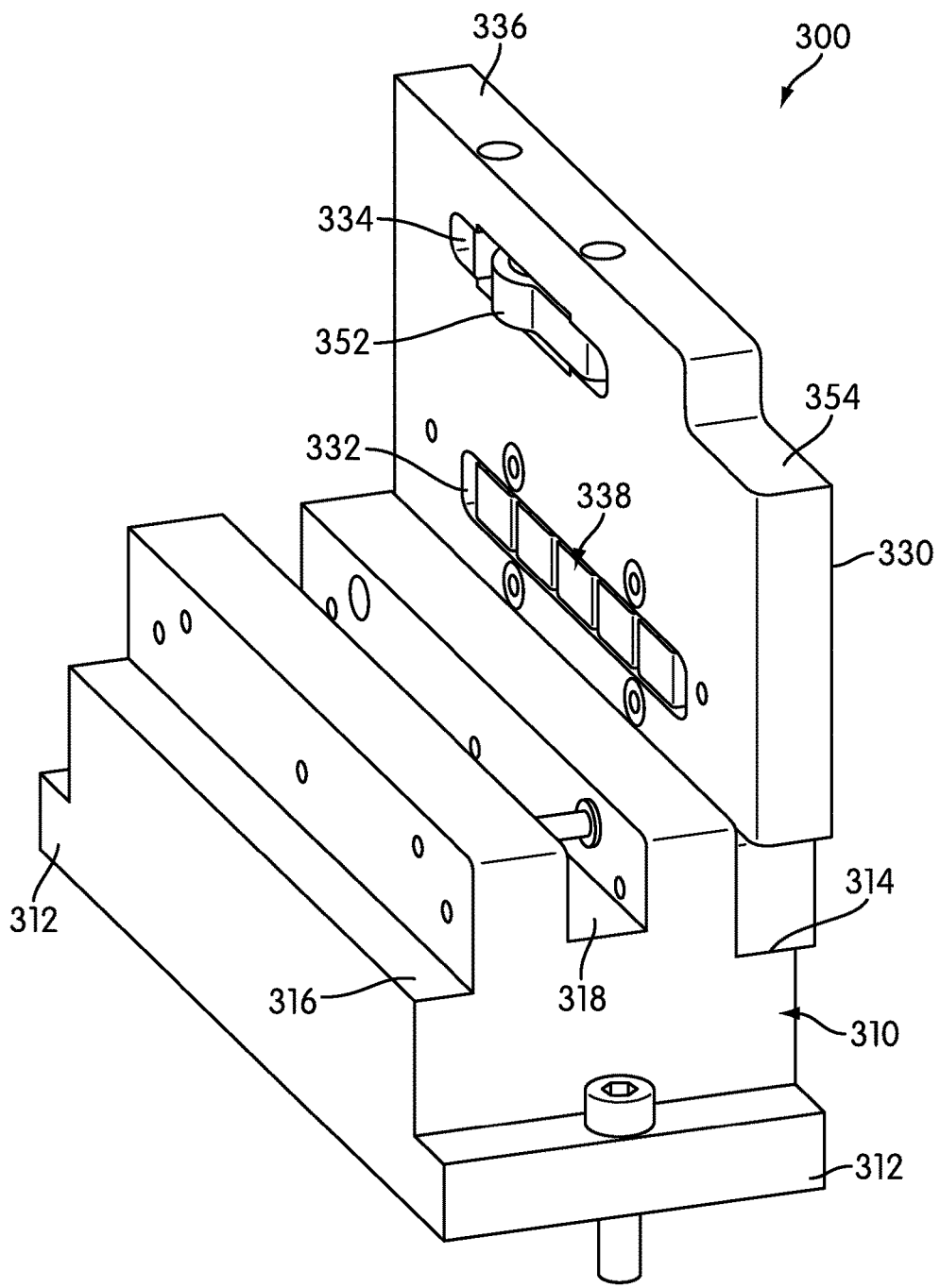
FIG. 18 is a partial front perspective of the receptacle holding station with various components of the receptacle holding station omitted from the figure.

The magnetic receptacle holding station and various components thereof are shown in FIGS. 16-19. As shown in FIGS. 16 and 17, a magnetic receptacle holding station 300 includes a base block 310 with a first wall 330, second wall 360, and third wall 368 secured to and, extending upwardly from the base block 310, and a shroud 370 partially covering the first, second, and third walls 330, 360, 368. A first receptacle slot 356 defined between first and second walls 330, 360 and a second receptacle slot 358 defined between second and third walls 360, 368 are each configured to receive an MRD 160, or other receptacle, as shown in FIG. 16. As shown in FIG. 18—in which the second wall 360, third wall 368, and shroud 370 are omitted—the base block 310 includes mounting flanges 312 for securing the receptacle holding station 300 to a datum plate, outer wall grooves 314, 316 for securing the first wall 330 and third wall 368, respectively, and a center slot 318 within which is secured the second wall 360. Base block 310 and walls 330, 360, 368 may be made from a suitable plastic, such as Delrin® acetal resin or PVC.

A grounding connector element 322 is secured to one of the mounting flanges 312.

Referring to FIG. 18, first wall 330 includes a magnet slot 332 formed therein along a lower portion thereof and a clip slot 334 formed therein along an upper portion thereof. A magnet subassembly 338 is mounted within the magnet slot 332 by mechanical fasteners, such as screws. A clip element 352 is mounted within the clip slot 334. A hook access corner cutout 354 is provided in the upper front corner of the first wall 330. Third wall 368 is substantially a mirror image of first wall 330 and includes a magnet slot within which a magnet subassembly is mounted and a clip slot within which a clip is mounted. In the illustrated embodiment, third wall 368 does not include a hook access cutout. Second wall 360 includes a magnet slot 362 within which a magnet subassembly 364 is mounted. A partial corner hook access cutout 366 is provided at the upper front portion of the second wall 360.

Shroud 370 includes a top panel 372, side panels 374, and a back panel 376 (see FIG. 17). Shroud 370 may be formed from an suitable material, such as sheet metal. Shroud 370 is secured to the first and third walls 330, 368, and a grounding connector 320 is secured to one side 374 of the shroud 370.

Figure 19:
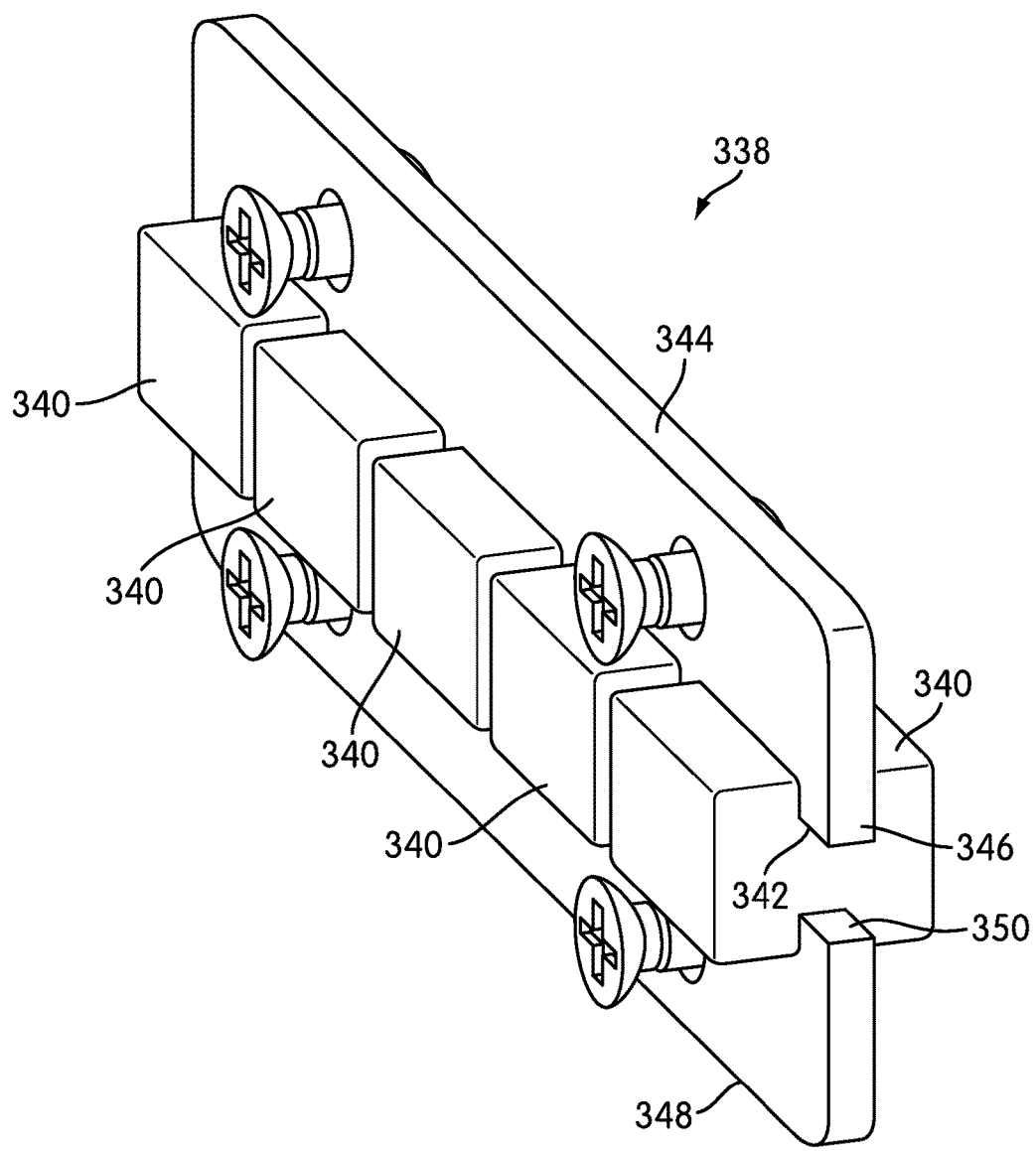
FIG. 19 is a perspective view of a magnet subassembly of the magnetic receptacle holding station.

Referring to FIG. 19, the magnet subassembly includes a plurality of magnets 340 (five in the illustrated embodiment), each being of a generally solid rectangular shape. An upper holder plate 344 is disposed within holder plate grooves 342 formed within the top surface of each of the magnets 340. Upper holder plate 344 includes a separating projection 346 at each end thereof and between adjacent magnets 340 to hold each magnet within its respective position. Similarly, the magnet subassembly 338 includes a lower holder plate 348 which is received within holder plate grooves formed in the lower surfaces of the magnets 340 and which includes a separating projection 350 at opposite ends thereof and between the adjacent magnets 340.

A receptacle, such as an MRD 160, can be placed within the receptacle holding slot 356 or 358 and supported on the upper edges 336 of the opposed first and second walls or second and third walls. Clip 352, which may comprise a resilient projection extending into the slot 356, releasably secures the MRD 160 within the slot. The hook access cutouts 354, 366 permit a manipulating hook (not shown) to be positioned alongside the manipulating structure 166 of the MRD 160 and to engage the manipulating structure 166 in the direction A as shown in FIG. 3.

An MRD 160 containing a sample material and a target capture reagent including magnetically-responsive solid supports can be placed within one of the slots 356, 358 of the magnetic receptacle holding station 300, and retained therein for a specified dwell time while the magnetically-responsive solid supports are drawn out of solution by the magnets of the magnetic receptacle holding station 300. After the specified dwell time, the MRD 160 is moved from the magnetic receptacle holding station 300 to the magnetic separation station 800. By placing the MRDs 160 into the magnetic receptacle holding station 300 for a specified dwell time prior to moving the MRDs 160 into the magnetic separation station 800, the amount of magnetic dwell time required in the magnetic separation station 800 can be reduced, thereby reducing the amount of time that each MRD 160 must spend in the magnetic separation station 800 and improving overall instrument throughput.

A magnetic receptacle holding station 300 shown in FIGS. 16-18 is for illustration purposes only. It should be recognized that a receptacle holding station embodying aspects of the present invention may have less than or more than three upright walls and two receptacle holding slots defined between opposed walls.

Transport Mechanism

An embodiment of a transport mechanism suitable for moving a receptacle, such as the MRD 160, into and out of the magnetic separation station 800 and the magnetic receptacle holding station 300 and between the magnetic separation station 800 and the magnetic receptacle holding station 300 will now be described.

Figure 20:
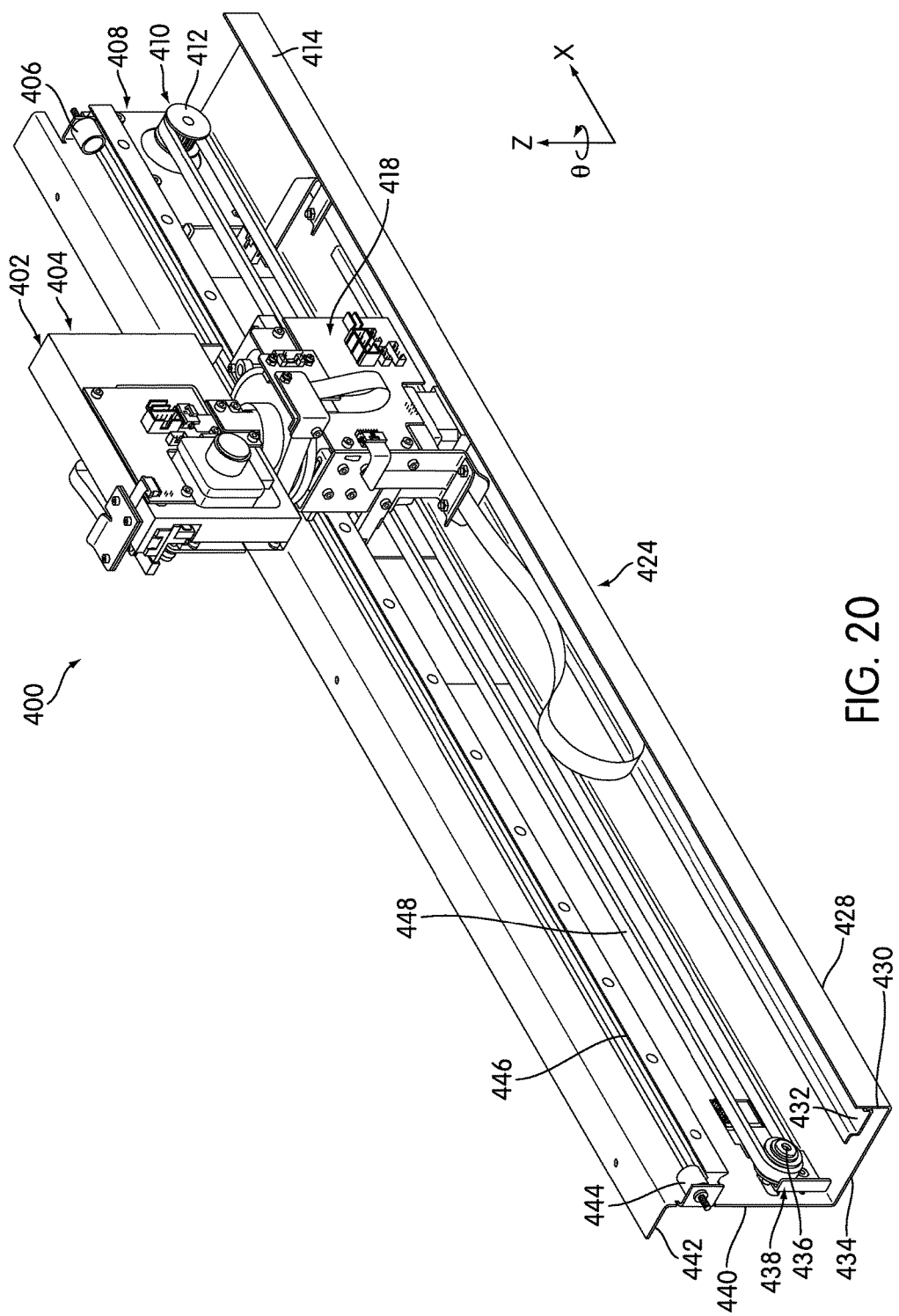
FIG. 20 is a perspective view of a receptacle transfer apparatus in the form of a receptacle distributor suitable for use in conjunction with embodiments of the present invention.

As shown in FIG. 20, a receptacle transfer apparatus in the form of a receptacle distributor 400 comprises a receptacle carrier assembly 402 which translates along a transport track assembly 408 in an "X" direction" under the power of an X-translation system (described below). The receptacle carrier assembly 402 includes a receptacle distribution head 404 configured to carry a reaction receptacle, such as an MRD 160, supported on a carrier assembly carriage 418 constructed and arranged to effect Z-axis translation and Θ rotation of the distribution head 404. In the illustrated embodiment, the track assembly 408 is linear (i.e., straight) and substantially horizontal, but in other embodiments, the track assembly is non-linear (i.e., at least partially curved) and/or non-horizontal (i.e., at least a portion of the track assembly is inclined or vertical).

In the illustrated embodiment, track assembly 408 comprises a generally "L" shaped channel 424 comprising a base portion 434—oriented substantially horizontally in the illustrated embodiment—and an upright backing 440 extending in an upright manner—oriented substantially vertically in the illustrated embodiment—from one edge of the horizontal base 434. A stiffening flange 430 extends upright from an edge of the base portion 434 opposite the upright backing 440, and a stiffening flange 442 extends laterally from an upper edge of the upright backing 440. A guide rail 446 is mounted to the upright backing 440 and extends in a parallel orientation with respect to the base portion 434. A cable guide track 432 is mounted to the base portion 434.

An X-translation system 410 comprises a drive, or transmission, belt 448 trained over a driven pulley 412 disposed on one side of the upright backing 440 at a distal end 414 of the channel 424 and over an idler pulley 436 disposed on the same side of the upright backing 440 at a proximal end 428 of the channel 424 and attached at opposite ends thereof to the carrier assembly carriage 418. Driven pulley 412 is operatively coupled to a carrier translation motor (not shown) mounted to an opposite side of the upright backing 440. A rotational encoder (not shown) is coupled to the drive motor.

The drive belt 448 is preferably equipped with a belt tensioner 438. Belt tensioner 438 comprises a sliding pulley mount, on which is mounted the idler pulley 436, and a spring. The pulley mount is slidably supported by the upright backing 440, but can be selectively fixed with respect to the upright backing 440 by a fastener element to prevent sliding of the mount. The spring urges the pulley mount in belt-tightening direction when the pulley mount 436 is not fixed with respect to the upright backing 440.

The distribution head 404 of the carrier assembly 402 is carried along the transport track assembly 408 by the carrier assembly carriage 418. The carrier assembly carriage 418 engages the guide rail 446, and translates along the transport track assembly 408. Rubber bumpers 444, 406 may be provided at opposite ends of the guide rail 446 to absorb contact by the carriage 418. Movement of the carrier assembly carriage 418 along the guide rail 446 is effected by the drive belt 448. When the carrier translation motor rotates the driven pulley 412 in a counter-clockwise fashion, the carrier assembly 402 is moved in a first X direction (to the left in the illustrated embodiment) towards the proximal end 428 of transport track assembly 408. Similarly, when the carrier translation motor rotates driven pulley 412 in a clockwise fashion, the carrier assembly 402 translates in a second X direction (to the right in the illustrated embodiment) towards the distal end 414 of transport track 408 assembly.

Figure 21:
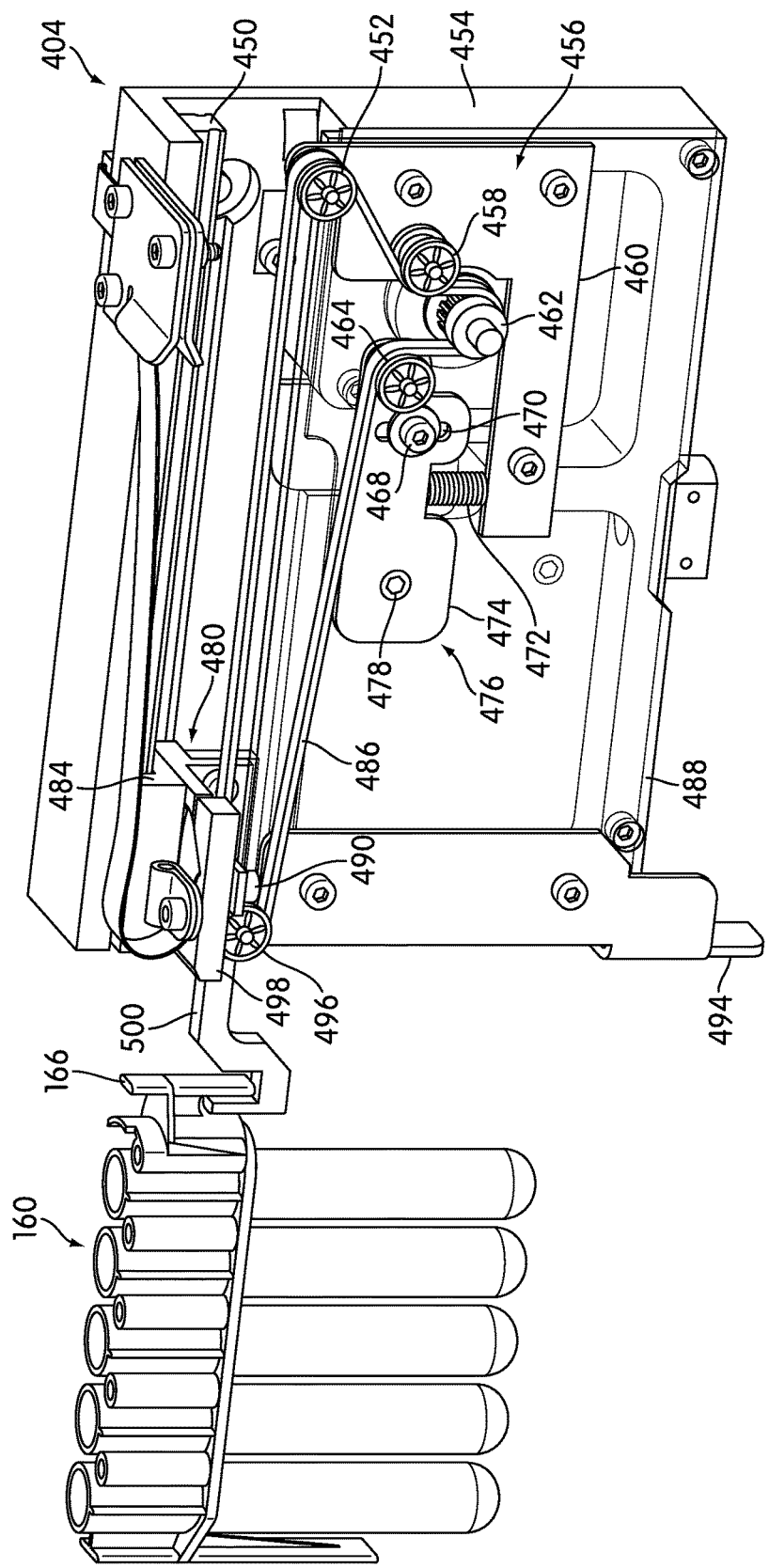
FIG. 21 is a perspective view of the receptacle distribution head and a hook actuator system in an extended position.

Details of the distribution head 402 are shown in FIG. 21. Distribution head 402 includes a distribution frame 454 that is supported for rotation about a vertical axis of rotation by the carrier assembly carriage 418. A side panel 488 is attached to one side of the distribution head frame 454. Side panel 488 may be transparent so that the interior of the distribution head 402 is visible. Distribution head 402 further includes a receptacle hook 500 configured to engage the manipulating structure 166 of an MRD 160. Devices other than a hook for engaging the receptacle and enabling physical manipulation of the engaged receptacle may be substituted.

A hook actuator system 456 effects linear translation (in the R direction relative to the Z-axis and the Θ direction) of the receptacle hook 500 between an extended position, as shown in FIG. 21, and a retracted position in which the MRD 160 is withdrawn into the distribution head 402. The hook actuator system 456 includes a hook carriage 480 to which the receptacle hook 500 is attached. A drive belt 486 is attached to the hook carriage 480 by a screw and bracket indicated at 490. Drive belt 486 is carried on a drive wheel 462 and idler wheels 464, 496, 452, 458. Idler wheels 452 and 458 are attached to a fixed idler wheel bracket 460, and idler wheel 496 is attached to an upper portion of a door engagement bracket 494 exterior to panel 488.

Door engagement bracket 494 may be provided for opening a door covering the loading slot 804. The door, which may be a pivoting, sliding, or rotating door, will include an arm or other projection depending from a portion of the door. In one embodiment, the distribution head 402 is positioned with the lower end of the door engagement bracket 494 in contact with the arm, and a slight X and/or Θ movement of the distribution head 402 is effected to move the door from a closed to an open position. The door is preferably spring-biased in a closed position, so that that when the arm is released from contact with the door engagement bracket 494, the door will spring back to the closed position.

Drive wheel 462 is attached to an output shaft of a drive motor (not shown) (preferably a stepper motor) which is mounted to an opposite side of the distribution frame 454. A rotational encoder (not shown) is attached to the drive motor. Drive wheel 462 preferably has a diameter of 9.55 mm resulting in a resolution of 0.15 mm per full motor step. The encoder had a resolution of 200 counts/revolution (A-B signals) resulting in a quadrupled resolution of 800 counts/revolution.

The hook actuator system 456 preferably includes a belt tensioner 476 for maintaining proper tension in the belt 486. Belt tensioner 476 includes a pivoting idler wheel bracket 474 to which idler wheel 464 is attached and which is pivotally attached to the side panel 488 by a pivot screw 478. A slot 470 is formed in an end of the pivoting idler wheel bracket 474, and a position lock screw 468 extends through the slot 470 into the side panel 488. A spring 472 is disposed between a portion of the pivoting idler wheel bracket 474 and the fixed idler wheel bracket 460. Tension in the belt 486 can be adjusted by loosening the position lock screw 468, thereby allowing the spring 472 to pivot the pivoting idler wheel bracket 474 and thus urge the idler wheel 464 upwardly to create the proper tension in the drive belt 486. When proper tension is achieved in the drive belt 486, the position lock screw 468 can thereafter be retightened.

The hook carriage 480 includes a rail channel 484 that translates along a hook carriage guide rail 450 attached to an upper portion of the distribution head frame 454. The receptacle hook 500 is attached to an insulation mount 498 disposed between the rail channel 484 and the hook 500 to electrically isolate the hook 500 from the distribution head 402 to facilitate capacitive sensing of contact by the hook 500 with another structural element of, e.g., the magnetic separation station 800 or the receptacle holding station 300.

Further details of the receptacle distributor can be found in U.S. Patent Application No. 61/178,728, the disclosure of which is incorporated by reference.

Figure 22:
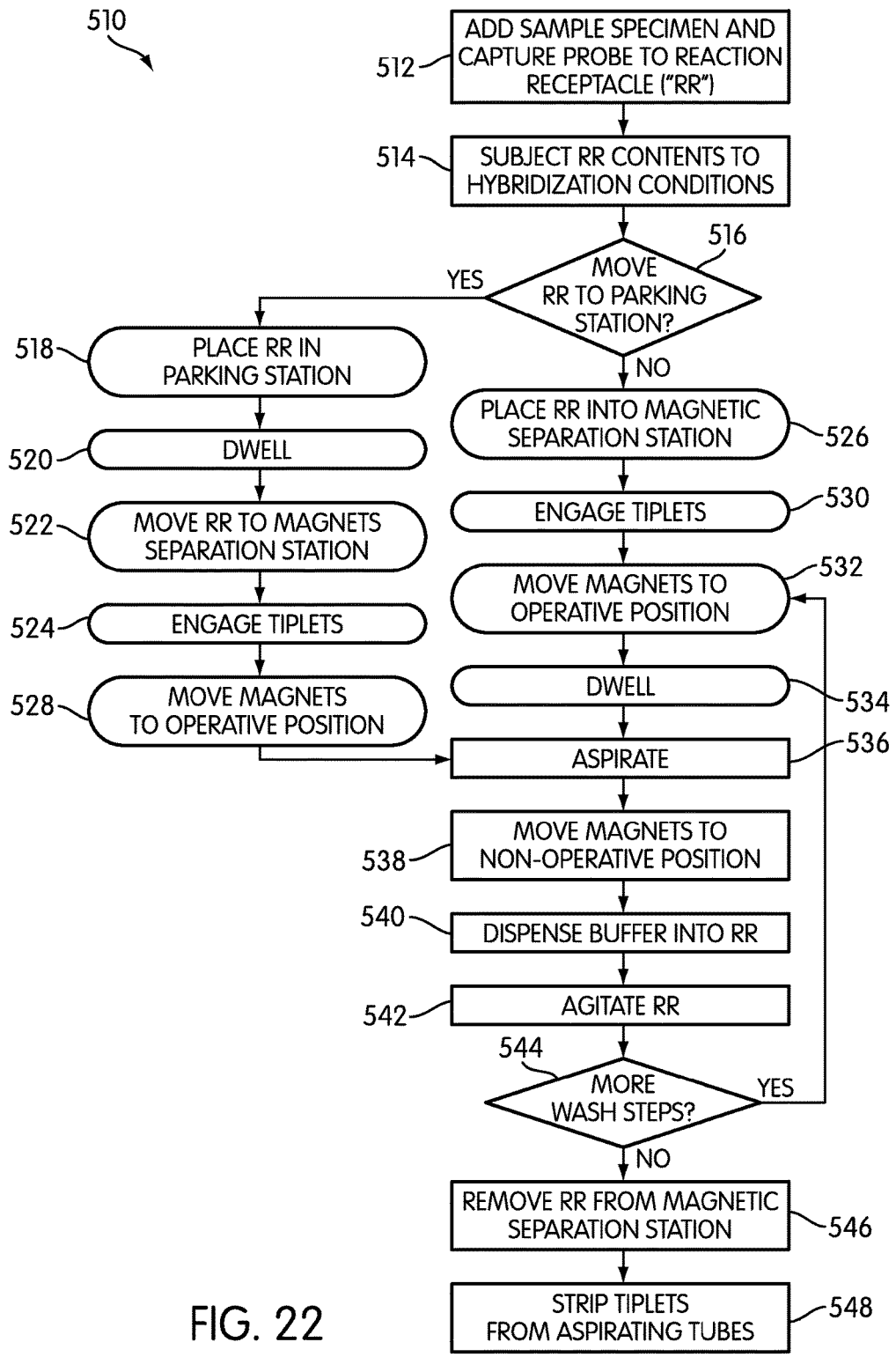
FIG. 22 is a flow chart illustrating a procedure for separating or isolating an analyte of interest (e.g., a target nucleic acid) from other components of a sample employing magnets and magnetically-responsive solid supports.

A procedure for separating or isolating an analyte of interest, such as a target nucleic acid, from other components of a sample is represented by process 510 shown in FIG. 22. The process begins at step 512 with a specimen preparation procedure whereby sample specimen and a target capture reagent including magnetically-responsive solid supports are added to a receptacle device (a single receptacle or multiple receptacles, e.g., the MRD 160). The sample specimen and target capture reagent may be added to the receptacle device by any means known in the art, including manual and automated means.

In step 514, the receptacle device containing the sample specimen and target capture reagent is subjected to conditions sufficient to cause the analyte of interest to be immobilized on the magnetically-responsive solid support. The conditions may include incubation of the receptacle device and its contents at one or more prescribed temperatures for prescribed periods of time. Procedures for immobilizing targeted nucleic acids on magnetically-responsive solid supports are exemplified in U.S. Pat. No. 6,534,273 and U.S. Patent Application Publication No. 2008-0286775.

In step 516, a decision is made as to whether to (1) move the receptacle device to a magnetic receptacle holding station 300 prior to moving the receptacle device to the magnetic separation station 800 or (2) move the receptacle device directly into a magnetic separation station 800.

If the decision is made to omit placing the receptacle device in the magnetic receptacle holding station 300, then, in step 526, the receptacle device is placed in the magnetic separation station 800, preferably using a receptacle transport mechanism, such as receptacle distributor 400 described above.

In step 530, with the receptacle device supported by the receptacle carrier unit 820 of the magnetic separation station 800, the receptacle carrier unit 820 is positioned to align each aspirator tube 860 with a tip 170 carried on the receptacle device, and each aspirator tube 860 is lowered until it is inserted into and frictionally engages a tip 170. In alternative embodiments, the tips are not carried on the receptacle device but are otherwise provided to each aspirator tube 860.

In step 532, magnets, which are initially in an inoperative position with respect to the receptacle device when the receptacle device is first placed into the magnetic separation station 800 in step 526, are moved to an operative position with respect to the receptacle device to draw magnetically-responsive solid supports toward the side of the receptacle device. In step 534, the receptacle device is held stationary in the receptacle carrier unit 820 with the magnets in an operative position for a specified dwell period (in one embodiment, 120 seconds) sufficient to draw a substantial portion of the magnetically-responsive solid supports to the side wall of the receptacle device and out of suspension.

In step 536, after performing a procedure to verify the presence of a tip 170 on each aspirator tube 860, the receptacle carrier unit 820 is moved to position each receptacle below an associated aspirator tube 860, each aspirator tube 860 is lowered into the associated receptacle, and fluid is aspirated from the receptacle in step 536, preferably while the magnets are maintained in the operative position with respect to the receptacle device.

In step 538, the magnets are moved to a non-operative position with respect to the receptacle device so that the magnetically-responsive solid supports of the target capture reagent will not be influenced by the magnetic force of the magnets.

In step 540, a wash solution is dispensed into each receptacle (e.g., 1 mL of wash buffer), and, in step 542, the receptacle device is agitated to dislodge the magnetically-responsive solid supports from the walls of the receptacle device and to re-suspend the magnetically-responsive solid supports.

In step 544, a decision is made as to whether additional wash steps must be performed. Depending on the procedure protocol, the wash procedure may be repeated one or more times. In one embodiment, 2 wash cycles are performed. If the wash procedure is to be repeated, the process returns to step 532, and steps 532 through 542 are repeated. If no further wash steps are to be performed, the receptacle device is removed from the magnetic separation station 800 in step 546.

In step 548, the tip 170 is stripped from each aspirator tube 860, and the magnetic separation station 800 is now ready to receive the next receptacle device to perform the magnetic separation wash process.

If, at step 516, the decision was made to place the receptacle device in the receptacle holding station 300 prior to moving it to the magnetic separation station 800, in step 518 the receptacle device is placed in the receptacle holding station 300, preferably using a receptacle transport mechanism, such as receptacle distributor 400 described above.

In step 520, the receptacle device is allowed to sit in the magnetic receptacle holding station 300 for a specified dwell period (in one embodiment, 580 seconds) sufficient to draw a substantial portion of the magnetically-responsive solid supports to the walls of the receptacle device and out of suspension.

In step 522, after the specified dwell period, and assuming the availability of a magnetic separation station 800, the receptacle device is moved from the receptacle holding station 300 to the magnetic separation station 800, using, for example, the receptacle distributor 400 described above. In one embodiment, the transfer from the receptacle holding station 300 to the magnetic separation station occurs in 4 seconds.

In step 524, each aspirator tube 860 is engaged with a tip 170 as described above in connection with step 530.

In step 528, magnets, which are initially in an inoperative position with respect to the receptacle device when the receptacle device is first placed into the magnetic separation station 800 in step 522, are moved to an operative position with respect to the receptacle device. As the magnetically-responsive solid supports of the target capture probe contained in the receptacle device have already been subjected to a magnetic force for a specified dwell period within the magnetic receptacle holding station 300 in step 520, an initial magnetic dwell period within the magnetic separation station 800 can be substantially shortened, or omitted altogether. That is, if the contents of the receptacle device are not agitated, a substantial portion of the solid supports will remain aggregated to the side of the receptacle device while the receptacle device is transferred from the receptacle holding station to the magnetic separation station. In experiments, the inventors have determined that the initial magnetic dwell can be reduced by 180 seconds by use of the magnetic receptacle holding station 300 (initial dwell of 300 seconds without first placing the receptacle device in the magnetic receptacle holding station as compared to 120 second initial magnetic dwell when the receptacle device is first placed in the magnetic receptacle holding station for 580 seconds).

The process next proceeds to step 536, and fluid is aspirated from the receptacle device while the magnetically-responsive solid supports are held to the walls of the receptacle device by the magnets. The process then proceeds through steps 540 through 548 as described above—returning, as desired, to step 532 to repeat steps 532-542.

While the present invention has been described and shown in considerable detail with reference to certain illustrative embodiments, those skilled in the art will readily appreciate other embodiments of the present invention. Accordingly, the present invention is deemed to include all modifications and variations encompassed within the spirit and scope of the following appended claims.

The invention claimed is:

1. An apparatus comprising:
   a fluid transfer device comprising a plurality of aspirator probes, each aspirator probe having a distal end, and each distal end being adapted to have a conduit mounted thereon;
   a slide configured for linear translation between a first position and a second position in the apparatus and having a bottom plate comprising a plurality of conduit stripping elements formed therein, the slide including a first wall and a second wall extending upwardly from the bottom plate and defining a slot between the first and second walls, wherein the slot is configured to receive the plurality of aspirator probes, and wherein the plurality of conduit-stripping elements are disposed in a bottom surface of the slot each conduit-stripping element being associated with a corresponding one of the plurality of aspirator probes, and each conduit-stripping element being adapted to remove a conduit from the distal end of an associated aspirator probe that is aligned with the conduit-stripping element, wherein the plurality of conduit-stripping elements are movable with the slide, such that when the slide is in the first position, no conduit-stripping element is aligned with an aspirator probe to strip the conduit mounted thereon, and when the slide is in the second position, each conduit-stripping element is aligned with the associated aspirator probe, and wherein each conduit stripping element comprises a key-hole opening having a first portion with a transverse size sufficient to permit the conduit to pass therethrough and a second portion with a transverse size sufficient to permit the probe to pass therethrough, but not sufficient to permit the conduit to pass therethrough; and a controller configured to:
cause the fluid transfer device to pass the distal end of the probe with the conduit disposed thereon through the first portion of the key-hole opening;
effect a linear translation of the slide so that the probe is in the second portion of the key-hole opening; and
withdraw the probe from the key-hole opening, the conduit being retained by the conduit-stripping element when the conduit is unable to pass through the second portion of the key-hole opening.

2. The apparatus of claim 1, further comprising a receptacle carrier configured to carry a receptacle device in an operative position with respect to the aspirator probes, wherein the receptacle carrier includes an orbital mixer assembly configured to impart an orbital motion to a receptacle device carried by the receptacle carrier.

3. The apparatus of claim 2, wherein the receptacle device comprises a plurality of receptacles, each receptacle being associated with one of the plurality of aspirator probes.

4. The apparatus of claim 1, wherein said fluid transfer device further comprises a probe moving mechanism adapted to move the plurality of aspirator probes in unison with respect to the associated receptacles.

5. The apparatus of claim 1, further comprising a guide structure for supporting said slide for linear translation between said first and second positions and a slide moving mechanism adapted to effect powered linear translation of said slide between said first and second positions.

6. The apparatus of claim 5, wherein said slide moving mechanism comprises:
a motor;
a threaded drive screw coupled to an output shaft of said motor; and
a screw follower mounted to said slide, wherein said drive screw is engaged with said screw follower such that powered rotation of said drive screw by said motor causes linear translation of said slide.

7. The apparatus of claim 5, wherein said slide moving mechanism comprises:
a motor with a drive pulley mounted to an output shaft thereof;
an idler pulley; and
a drive belt carried on said drive pulley and said idler pulley and attached to said slide to transfer powered rotation of said drive pulley to linear translation of said slide.

8. The apparatus of claim 1, comprising a plurality of said aspirator probes, wherein the conduit-stripping elements are arranged in a staggered configuration so that when the plurality of aspirator probes are moved with respect to the plurality of conduit-stripping elements, the conduit-stripping elements sequentially remove the conduits from the associated aspirator probes one at a time.

9. The apparatus of claim 1, further comprising one or more magnets carried by the slide.

10. A method for removing a conduit from a distal end of each of a plurality of fluid transfer probes, comprising:

effecting powered linear translation of a slide in a direction transverse to the axes of the probes to move conduit-stripping portions of the slide from first locations to second locations, wherein the slide includes a bottom plate comprising the plurality of conduit stripping portions formed therein, the slide including a first wall and a second wall extending upwardly from the bottom plate and defining a slot between the first and second walls, wherein the slot is configured to receive the plurality of aspirator probes, wherein when the conduit-stripping portions are in the first locations, no conduit-stripping portion is in a position to be engaged by any of the probes, and when the conduit-stripping portions are in the second locations, the conduit-stripping portions are in positions to be engaged by the distal ends of the probes and are disposed beneath a receptacle device positioned so as to be engageable by the probes:

removing the receptacle device from the position in which it is engageable by the probes:

and with the conduit-stripping portions in the second locations, effecting powered axial movement of the probes with respect to the slide to engage the distal ends of the probes with the conduit-stripping portions of the slide and strip the conduits from the probes, wherein stripping the conduits from the distal ends of the probes comprises:

providing, for each conduit-stripping portion, a key-hole opening having a first portion with a transverse size sufficient to permit the conduit to pass therethrough and a second portion with a transverse size sufficient to permit the probe to pass therethrough, but not sufficient to permit the conduit to pass therethrough;

passing the distal end of the probe with the conduit disposed thereon through the first portion of the key-hole opening;

effecting a linear translation of the slide so that the probe is in the second portion of the keyhole opening; and withdrawing the probe from the key-hole opening, the conduit being retained by the conduit-stripping portion when the conduit is unable to pass through the second portion of the keyhole opening.

11. The method of claim 10, wherein stripping the conduits from the distal ends of the probes comprises moving the probes in an axial direction toward the slide until the conduits disposed on the distal ends of the probes engage the conduit-stripping portions of the slide and then moving the probes in an opposite axial direction away from the slide while retaining the conduits with the conduit-stripping portions of the slide to pull the conduits from the distal ends of the probes.

12. The method of claim 10, comprising sequentially retaining each of the conduits during axial movement of the probes away from the slide so that all conduits are not pulled from the distal ends of the probes simultaneously.

13. The method of claim 10, wherein one or more magnets are carried on the slide such that, when the slide is in the first location, the magnets have substantially no effect on magnetically-responsive solid supports contained in a receptacle device positioned so as to be engageable by the probes, and when the slide is in the second location, the magnets are positioned adjacent to the receptacle device so that the magnets will draw at least a portion of the magnetically-responsive solid supports to a wall of the receptacle device.

14. The method of claim 13, wherein the magnetically-responsive solids supports are adapted to immobilize an analyte thereon.

* * * * *